United States Patent
Tedford

(10) Patent No.: US 12,390,658 B2
(45) Date of Patent: Aug. 19, 2025

(54) METHODS FOR TREATING OCULAR DISEASE

(71) Applicant: LumiThera, Inc., Poulsbo, WA (US)

(72) Inventor: Clark E. Tedford, Poulsbo, WA (US)

(73) Assignee: LumiThera, Inc., Poulsbo, WA (US)

( * ) Notice: Subject to any disclaimer, the term of this patent is extended or adjusted under 35 U.S.C. 154(b) by 0 days.

(21) Appl. No.: 16/761,078

(22) PCT Filed: Nov. 2, 2018

(86) PCT No.: PCT/US2018/059072
§ 371 (c)(1),
(2) Date: May 1, 2020

(87) PCT Pub. No.: WO2019/090159
PCT Pub. Date: May 9, 2019

(65) Prior Publication Data
US 2021/0178178 A1    Jun. 17, 2021

Related U.S. Application Data

(60) Provisional application No. 62/663,535, filed on Apr. 27, 2018, provisional application No. 62/580,972, filed on Nov. 2, 2017.

(51) Int. Cl.
*A61N 5/06*    (2006.01)

(52) U.S. Cl.
CPC ...... *A61N 5/0613* (2013.01); *A61N 2005/066* (2013.01); *A61N 2005/0663* (2013.01)

(58) Field of Classification Search
CPC ............ A61F 9/008; A61F 2009/00863; A61F 2009/00885; A61N 5/0613; A61N 2005/066; A61N 2005/0663
See application file for complete search history.

(56) References Cited

U.S. PATENT DOCUMENTS 9,062,105 B1    6/2015    Clube
9,592,404 B2    3/2017    Dotson et al.
(Continued)

FOREIGN PATENT DOCUMENTS

WO    WO2016040534 A1 *    3/2016    ............. A61F 13/00

OTHER PUBLICATIONS

Merry, G. F., Munk, M. R., Dotson, R. S. , Walker, M. G. , Devenyl, R. G. (2016). Photobiomodulation reduced drusen volume and improves visual activity and contrast sensitivity in dry-age related macular degeneration. Acta Opthalmologica, 95(4). (Year: 2016).*
(Continued)

*Primary Examiner* — Lynsey C Eiseman
*Assistant Examiner* — Skylar Lindsey Christianson
(74) *Attorney, Agent, or Firm* — Seed Intellectual Property Law Group LLP

(57) ABSTRACT

Methods for treating ocular diseases such as dry age-related macular degeneration include administering non-invasive photobiomodulation light therapy in the context of a prior PBM treatment, on the basis of a subject response to prior PBM treatment, on the basis of a patient pre-treatment characteristic, and combinations thereof. In some embodiments, methods comprise administering PBM therapy to subjects who have received PBM about four to six months prior to the present administering. In some embodiments, methods comprise administering PBM therapy to subjects in early stages of dry age-related macular degeneration.

20 Claims, 17 Drawing Sheets

(56) References Cited

U.S. PATENT DOCUMENTS

| | | | |
|---|---|---|---|
| 2002/0183302 A1* | 12/2002 | Strong | A61K 41/0071 |
| | | | 604/20 |
| 2010/0150911 A1 | 6/2010 | Caiado De Castro Neto et al. | |
| 2015/0088231 A1 | 3/2015 | Rubinfeld et al. | |
| 2016/0067086 A1* | 3/2016 | Tedford | A61N 5/062 |
| | | | 606/4 |
| 2016/0317833 A1* | 11/2016 | Tedford | A61N 5/0613 |
| 2019/0192345 A1 | 6/2019 | Gast et al. | |
| 2021/0060354 A1 | 3/2021 | Eells et al. | |
| 2021/0178178 A1 | 6/2021 | Tedford | |

OTHER PUBLICATIONS

"Photobiomodulation for the Treatment of Retinal Diseases: A Review." International Journal of Ophthalmology, vol. 9, No. 1, 2016, https://doi.org/10.18240/ijo.2016.01.24. (Year: 2016).*

Scruggs, B. A. (n.d.). Age-related macular degeneration. The University of Iowa. Retrieved Sep. 30, 2022, from https://webeye.ophth.uiowa.edu/eyeforum/atlas/pages/AMD.htm#:~:text=AMD%20has%20been%20categorized%20by,no%20drusen%20without%20pigment%20changes. (Year: 2022).*

Merry, Graham, et al; Treatment of dry Age-related Macular Degeneration using Photobiomodulation; pp. 1-10; 2012. (Year: 2012).*

Chakravarthy et al., "Characterizing Disease Burden and Progression of Geographic Atrophy Secondary to Age-Related Macular Degeneration," *Ophthalmology* 125:842-849, 2018.

Chew et al., "Ten-Year Follow-up of Age-Related Macular Degeneration in the Age-Related Eye Disease Study: AREDS Report No. 36," *JAMA Ophthalmol.* 132(3):272-277, Mar. 2014.

Grossman et al., "780 nm Low Power Diode Laser Irradiation Stimulates Proliferation of Keratinocyte Cultures: Involvement of Reactive Oxygen Species," *Lasers in Surgery and Medicine* 22:212-218, 1998.

International Search Report and Written Opinion, mailed Jan. 22, 2019, for International Application No. PCT/US2018/059072. (8 pages).

Joachim et al., "The Incidence and Progression of Age-Related Macular Degeneration over 15 Years," *Ophthalmology* 122(12):2482-2489, Dec. 2015.

Karu et al., "Irradiation with He—Ne laser increases ATP level in cells cultivated in vitro," *Journal of Photochemistry and Photobiology* 27:219-223, 1995.

Karu et al., "Cellular Effects of Low Power Laser Therapy Can be Mediated by Nitric Oxide," *Lasers in Surgery and Medicine* 36:307-314, 2005.

Karu et al., "Exact Action Spectra for Cellular Responses Relevant to Phototherapy," *Photomedicine and Laser Surgery* 23(4):355-361, 2005.

Labrique et al., "A novel device for assessing dark adaptation in field settings," *BMC Ophthalmology* 15:74, 2015. (9 pages).

Nita et al., "The Role of the Reactive Oxygen Species and Oxidative Stress in the Pathomechanism of the Age-Related Ocular Diseases and Other Pathologies of the Anterior and Posterior Eye Segments in Adults," *Oxidative Medicine and Cellular Longevity 2016*(Article ID 3164734), 2016. (24 pages).

Sadda et al., "Consensus Definition for Atrophy Associated with Age-Related Macular Degeneration on OCT: Classification of Atrophy Report 3," *Ophthalmology*, 2017. (12 pages).

Schmitz-Valckenberg et al., "Semiautomated Image Processing Method for Identification and Quantification of Geographic Atrophy in Age-Related Macular Degeneration," *Invest. Ophthalmol. Vis. Sci.* 52(10):7640-7646, Sep. 2011.

Slakter et al., "Digital Algorithmic Diabetic Retinopathy Severity Scoring System (An American Ophthalmological Society Thesis)," *Trans. Am. Ophthalmol. Soc.* 113:T9[1]-T9[18], 2015.

Wong et al., "Global prevalence of age-related macular degeneration and disease burden projection for 2020 and 2040: a systematic review and meta-analysis," *Lancet Glob. Health* 2:e106-e116, Feb. 2014.

Wong-Riley et al., "Photobiomodulation Directly Benefits Primary Neurons Functionally Inactivated by Toxins," *The Journal of Biological Chemistry* 280(6):4761-4771, Feb. 11, 2005.

Wu et al., "Low-Luminance Visual Acuity and Micoperimetry in Age-Related Macular Degeneration," *Ophthalmology* 121(8):1612-1619, Aug. 2014.

Yehoshua et al., "Progression of Geographic Atrophy in Age-Related Macular Degeneration Imaged with Spectral Domain Optical Coherence Tomography," *Ophthalmology* 118(4):679-686, Apr. 2011. (18 pages).

Zhao et al., "Age-Related Retinopathy in NRF2-Deficient Mice," *PLoS One* 6(4):e19456, Apr. 2011. (10 pages).

Friberg et al., "Is Drusen Area Really So Important? An Assessment of Risk of Conversion to Neovascular AMD Based on Computerized Measurements of Drusen," *IOVS* 53(4):1742-1751, Apr. 2012. (10 pages).

Ishikawa, "Abnormalities in Glutamate Metabolism and Excitotoxicity in the Retinal Diseases," *Hindawi Publishing Corporation, Scientifica*, vol. 2013, Article ID 528940, 2013. (13 pages).

Tang et al., "Photobiomodulation in the treatment of patients with non-center-involving diabetic macular oedema," *Br. J. Ophthalmol.* 98(8):1013-1015, Aug. 2014 (NIH Public Access Author Manuscript, available in PMC Aug. 1, 2014) (7 pages).

Tang, J. et al., "Low-Intensity Far-Red Light Inhibits Early Lesions That Contribute to Diabetic Retinopathy: In Vivo and In Vitro", IOVS, vol. 54, No. 5, May 2013, 10 pages.

Cheng, Y. et al., "Photobiomodulation Inhibits Long-term Structural and Functional Lesions of Diabetic Retinopathy", Diabetes, vol. 67, Feb. 2018, 8 pages.

Saliba, A. et al., "Photobiomodulation Mitigates Diabetes-Induced Retinopathy by Direct and Indirect Mechanisms: Evidence from Intervention Studies in Pigmented Mice", PLOS One 10(10), Oct. 1, 2015, 14 pages.

Eells et al., "Mitochondrial signal transduction in accelerated wound and retinal healing by near-infrared light therapy," *Mitochondrion* 4(5-6):559-567, 2004.

Light Bioscience, "Gentlewaves LED Photomodulation Device," downloaded from http://www.lightbioscience.com/led_device.html on Mar. 1, 2005, 1 page.

LumiThera, "Photobiomodulation for eye diseases," Selected Abstracts, Aug. 21, 2013. (24 pages).

Riverside Facial Plastic Surgery and Sinus Center, "Gentlewaves LED Photomodulation Fact Sheet," downloaded from http://www.riversideface.com/pages/gentlewaves.html on Mar. 9, 2015, 4 pages.

Tosk, "FDA Clears GentleWaves: The First and Only Light Emitting Diode Device for the Treatment of Periorbital Wrinkles and Rhytids," downloaded from http://www.drmcdaniel.com/fda-clears-gentlewaves on Mar. 9, 2015, 2 pages.

Bearse Jr. et al., "A multifocal electroretinogram model predicting the development of diabetic retinopathy", ScienceDirect, Progress in Retinal and Eye Research 25, 2006, 425-448.

Kauppinen et al., "Inflammation and its role in age-related macular degeneration", Cell Mol Life Sci. 2016, 73(9):1765-1786, 22 pages.

* cited by examiner

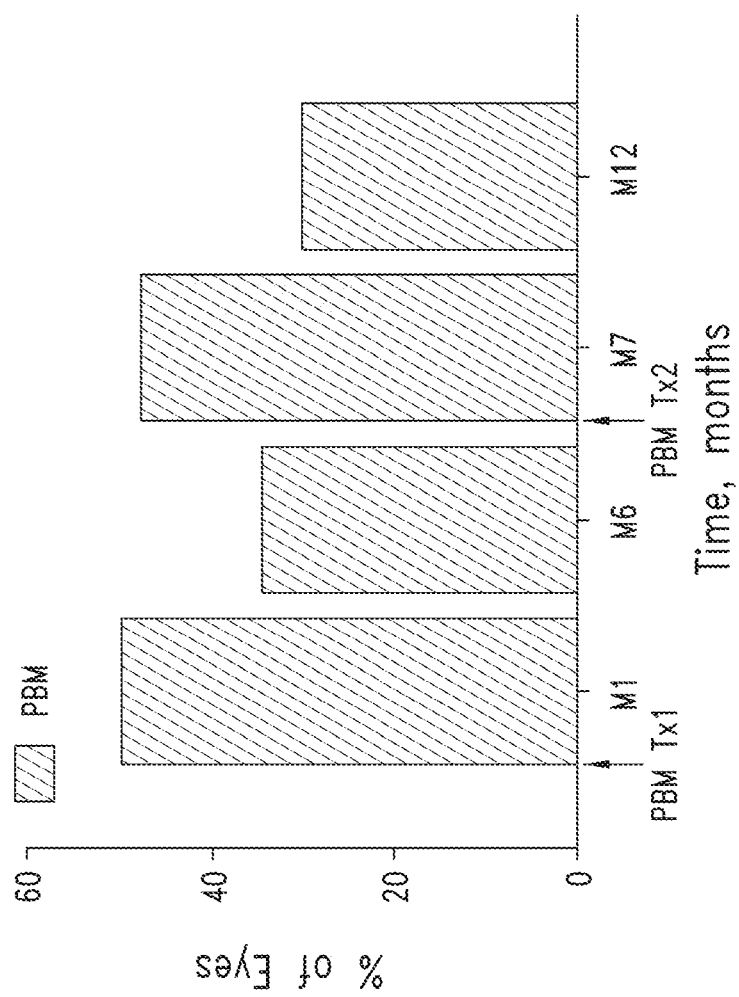

METHODS FOR TREATING OCULAR DISEASE

CROSS REFERENCE TO RELATED APPLICATIONS

This application claims the benefit under 35 U.S.C. § 119(e) to U.S. Provisional Application No. 62/580,972 filed Nov. 2, 2017, and U.S. Provisional Application No. 62/663,535, file Apr. 27, 2018, which applications are incorporated by reference herein in their entireties.

STATEMENT OF GOVERNMENT INTEREST

This invention was made with government support under National Eye Institute #3R43EY025508-01S1 awarded by the National Institutes of Health. The government has certain rights in the invention.

BACKGROUND

Age-related macular degeneration (AMD) is a retinal disease that results in irreversible, severe loss of vision, including legal blindness. Disease progression inevitably leads to significant visual dysfunction and serious compromises in quality of life (QoL). The prevalence of AMD is projected to affect 196 million by the year 2020 with expected growth to 288 million in 2040 (see Wong et al., Lancet Glob. Health 2(2):e106-e116 (2014)).

Progression of AMD is characterized by accumulation of membranous debrids, lipofuscin and extracellular material and complement deposition. The advanced late stage dry form of AMD, which accounts for 80-90% of the cases is characterized by retinal pigment epithelium (RPE) and outer retinal atrophy, whereas only 10-20% develop the exudative, wet late stage form, with choroidal neovascularization (CNV) as a hallmark of respective disease.

Current modalities for treating wet AMD include periodic intravitreal injections of Anti-VEGF (Vascular endothelial growth factor) compounds. The more frequent dry form of AMD has limited treatment options available other than lifestyle changes and the use of vitamin supplements demonstrating a significant unmet clinical need for alternate treatment plans for an expanding population base.

Accordingly, new modalities for treating dry AMD are needed. The presently disclosed embodiments address these needs and provide other related advantages.

BRIEF DESCRIPTION OF THE DRAWINGS

FIG. 5C shows the percentage of PBM-treated patients with a ≥5 letter improvement on ETDRS VA from BL over time.

DETAILED DESCRIPTION

Figure 1:
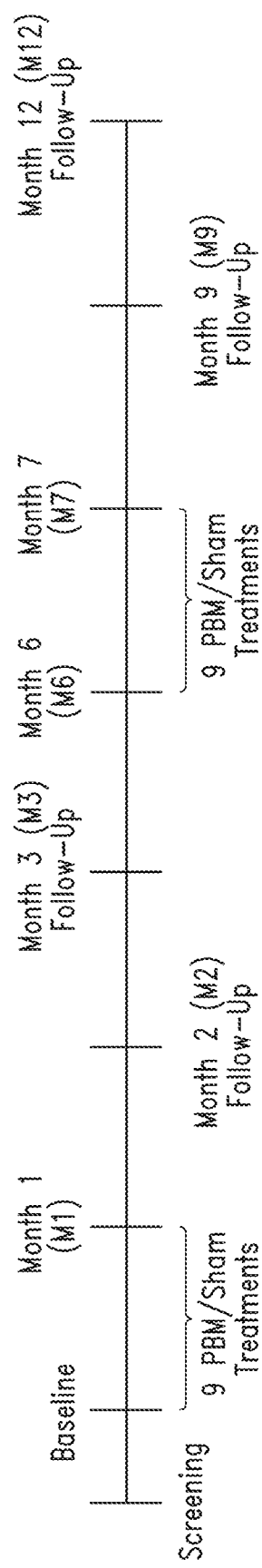
FIG. 1 shows a schematic illustration of a clinical study of the present disclosure investigating the use of photobiomodulation (PBM) to treat dry age-related macular degeneration (AMD), as described in the Examples.

In certain aspects, the present disclosure provides methods for treating ocular diseases (e.g., dry age-related macular degeneration (AMD), which methods comprise use of photobiomodulation therapy (PBM) in the red, yellow, and/or near-infrared light ranges.

In the presently disclosed clinical study, it was surprisingly determined that subjects who have previously received PBM therapy for dry AMD benefitted from a follow-on PBM treatment provided at least about M6 following an initial treatment.

Accordingly, in certain embodiments, methods are provided that comprise administering PBM therapy according to the present disclosure where a subject in need thereof has received an initial PBM therapy at least about 1, 2, 3, 4, 5, 6, or more (e.g., about 7, 8, 9, 10, or more) months prior to the present administration (e.g., a present administration can be a second or subsequent administration to a prior administration). In some embodiments, an initial PBM therapy was administered at least about 3, 4, 5, or 6 months prior to the present administration. In particular embodiments, an initial PBM therapy was administered at least about 5 or 6 months prior to the present administration.

In some embodiments, one or both of an initial and a follow-up PBM therapy comprise administering PBM 3, 4, 5, 6, 7, 8, 9, 10, or more times during a 3-4 week period (e.g., 2-3 or more times per week for 3-4 or more weeks). In certain embodiments, an initial and a follow-on PBM therapy comprise one or more PBM treatment that is the same (e.g., PBM of the same light(s), light intensity(ies), for the same duration, to the same eye(s), for the same number of sessions). In certain embodiments, an initial and a follow-on PBM therapy comprise one or more PBM treatment that is the same in all aspects. In some embodiments, a PBM treatment is administered that differs in at least one aspect (e.g., PBM of a different light(s), light intensity(ies), different durations, to a different eye(s), or for a different number of sessions, or any combination thereof) from a prior or initial PBM.

Furthermore, in some cases, the subjects benefitting most from PBM therapy were those who received the PBM treatment while in earlier stages of the disease; e.g., had better baseline vision or a less-advanced state of disease progression prior to treatment than those subjects who experienced lesser benefit following the PBM therapy regime. Accordingly, in some embodiments, a subject (or subject eye) selected for PBM therapy has a pre-treatment AREDS categorization of AREDS 1, 2, 3, or 4. In further embodiments, a subject (or subject eye) selected for PBM therapy has a pre-treatment AREDS categorization or classification of AREDS 2 or 3. In particular embodiments, a subject (or subject eye) selected for PBM therapy has a pre-treatment AREDS categorization of AREDS 3. In some embodiments, a subject (or subject eye) selected for PBM therapy has a pre-treatment best corrected visual acuity (BCVA) letter score of about 70, 71, 72, 73, 74, 75, 76, 77, 78, 79, 80, or more. In some embodiments, a subject (or subject eye) selected for PBM therapy has a pre-treatment BCVA letter score of at least about 74. In some embodiments, a subject (or subject eye) selected for PBM therapy has a pre-treatment BCVA letter score of at least about 80. In some embodiments, a subject (or subject eye) selected for or receiving PBM therapy does not have geographic atrophy (GA) with central foveolar involvement. In some embodiments, a subject selected for or receiving PBM therapy has a pre-treatment has a Snellen BCVA equivalent score of 20/100 or better.

In another aspect, treatment with PBM according to present disclosure may be determined or performed according to the type, degree, and/or duration of benefit achieved by a subject (e.g., selected for or identified as having one or more of the herein described criteria) to a prior or initial PBM therapy. For example, in some embodiments, a subject receives PBM therapy about 4-6 months following a prior or initial PBM therapy, wherein after about 1 month of receiving the prior PBM, the eye had an increase in a best corrected visual acuity (BCVA) letter score of 5 or more letters as compared to the BCVA letter score of the eye before receiving the prior PBM. In other embodiments, a method for treating dry age-related macular degeneration (dry AMD) in an eye of a subject, comprises administering to the eye an effective amount of photobiomodulation (PBM) comprising one or more of: (i) light having a wavelength in a yellow range; (ii) light having a wavelength in a red range; and (iii) light having a wavelength in a near-infrared (NIR) range, wherein the eye had received PBM about 1, 2, or 3 months prior, wherein after about 1 month of receiving the prior PBM, the eye had an increase a best corrected visual acuity (BCVA) letter score of less than 5 letters as compared to the BCVA letter score of the eye before receiving the prior PBM.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as size or thickness, or length of time (e.g., seconds, minutes, hours, days, weeks, months) are to be understood to include any integer within the recited range, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The terms "treat" and "treatment" refer to medical management of a disease, disorder, or condition of a subject (i.e., patient, host, who may be a human or non-human animal) (see, e.g., Stedman's Medical Dictionary). In general, an appropriate dose and treatment regimen according to the methods and compositions described herein results in a therapeutic or prophylactic benefit. Therapeutic or prophylactic benefit resulting from therapeutic treatment or prophylactic or preventative methods include, for example, an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated with the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

Subjects in need of the methods described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the methods described herein can be evaluated by design and execution of in vitro assays, preclinical studies, and clinical studies in subjects to whom administration of the compositions is intended to benefit, as described in the examples.

Treatment of an ocular disorder (e.g., dry AMD) in an eye or eyes can comprise an effect determinable using any of a number of clinically accepted metrics, including, for example: a statistically significant improvement in a best corrected visual acuity (BCVA) letter score according to an optometry chart (e.g., an ETDRS chart (Precision Vision, USA)) or a Snellen equivalent thereof; a statistically significant improvement in contrast sensitivity (CS) using, for example, the Functional Acuity Contrast Test (FACT), which can be performed using a chart that includes a series of grating patches with functionally different spatial frequencies; a statistically significant improvement in retinal sensitivity (RS) or fixation stability; e.g., as determined by microperimetry; a statistically significant decrease in the rate of growth, absolute growth, volume, thickness, number, or geographic spread of drusen (e.g., measurable using ocular coherence tomography such as SD-OCT, such as with a Spectralis OCT or TruTrack™ device (Heidelberg Engineering, Heidelberg, Germany)); or a statistically significant improvement in responses to one or more questions from the National Eye Institute VFQ-25 Questionnaire (e.g., Questions from Part II: Difficulty with activities; e.g., Q5-Q14); VFQ25 can be found online at, for example, https:/nei.nih.gov/sites/default/files/nei-pdfs/vfq_sa.pdf). It will be understood that a statistically significant response or improvement can be in response to any functional variant of a herein-described test (e.g., a question in a questionnaire can be differently worded than the specific language used in the VFQ-25, but is still within the scope of the present disclosure when it is substantively the same as a reference question in VFQ-25).

A "patient" or "subject" includes an animal, such as a human, dog, cat, monkey, ape, cow, horse, sheep, lamb, pig, chicken, turkey, quail, mouse, rat, rabbit or guinea pig. The animal can be a mammal, such as a non-primate or a primate (e.g., monkey, ape, and human). In some embodiments, a patient is a human, such as a human infant, child, adolescent, or adult, such as an adult about 20, 30, 35, 40, 45, 50, 55, 60, 65, 70, 75, 80, 85, 90, 95, 100, 105, or 110 years of age, or more.

As used herein, "administration" of a composition or therapy refers to delivering the same to a subject, regardless of the route or mode of delivery. Administration may be effected a single time, continuously (i.e., without stopping, or at regular intervals without a predetermined end), or intermittently. Administration may be for treating a subject already confirmed as having a recognized condition, disease or disease state, or for treating a subject susceptible to or at risk of developing such a condition, disease or disease state.

"Effective amount" or "therapeutically effective amount" refers to that amount of a PBM therapy described herein which, when administered to a mammal (e.g., human), is sufficient to aid in treating a disease. The amount of PBM therapy that constitutes an effective amount will vary depending on the condition to be treated and its severity, the manner of administration, and the age of the mammal to be treated, but can be determined routinely by one of ordinary skill in the art having regard to her own knowledge and to this disclosure. When referring to an individual active component (e.g., light of a PBM wavelength or wavelengths), administered alone, an effective dose refers to that component alone. When referring to a combination, an effective dose refers to combined amounts of the active components (e.g., light of different wavelengths) that result in the therapeutic effect, whether administered serially, concurrently or simultaneously.

Photobiomodulation (PBM) and PBM Therapy Parameters

"Photobiomodulation," also referred to as "PBM" herein, refers to the effect of visible light energy, typically of a wavelength from about 500 nm-1000 nm, to stimulate, suppress, or otherwise modulate a biological activity. PBM is distinguishable from other forms of light-based intervention, such as photoablating or photocoagulating lasers, in that it does not cause significant damage to (e.g., cauterize, ablate, coagulate, kill, or scar) to target cells or tissue. Without being bound by theory, PBM may act at the cellular level by activating mitochondrial respiratory chain components, resulting in stabilization of metabolic function. For example, it has been suggested that cytochrome C oxidase (CCO) is a key photoacceptor of light in the far red to near infrared spectral range. Grossman et al., *Lasers. Surg. Med.* 22:212-218 (1998); Kara et al., *J. Photochem. Photobiol. B.* 27:219-223 (1995); Karu and Kolyakov, *Photomed. Laser Surg.* 23:355-361 (2005); Kara et al., *Lasers Surg. Med.* 36:307-314 (2005); and Wong-Riley et al., *J. Biol. Chem.* 280:4761-4771 (2005).

Various ocular conditions can benefit from PBM, such as, for example, inflammatory eye conditions including trauma (e.g., related to or caused by a cataract or lens surgery, or a trabeculoplasty, or a procedure to reconnect a detached retina), age-related macular degeneration (dry and wet forms), glaucoma, diabetic retinopathy, retinitis pigmentosa, central serous retinopathy (CRS), non-arteritic anterior ischemic optic neuropathy (NAION), Leber's hereditary optic neuropathy disease, uveitis, or the like. Ocular disorders that can benefit with PBM include those characterized by ocular damage or degeneration. Ocular degeneration can include the process of cell destruction resulting from a primary destructive event such as ocular trauma or surgery, as well as from secondary, delayed and progressive destructive mechanisms that are invoked by cells due to the occurrence of a primary destructive or disease event. In certain embodiments, methods are provided for treating retinal disorders. In some embodiments, methods are provided for treating dry age-related macular degeneration.

Typically, PBM for treating ocular conditions involves delivering light energy from an external light-emitting source to the eye of a subject or patient, wherein the light energy comprises one or more PBM wavelengths and is delivered with sufficient intensity (e.g., power density or irradiance, which may be measured at a target tissue, or an emission source, or at any point there between. Standard measurements in this regard include $J/cm^2$ and $mW/cm^2$. Determination of an appropriate power output to deliver light of appropriate energy(ies) and wavelength(s) to a target of interest can be performed using calculations and methods described in, for example, PCT Publication No. WO 2016/040534A1. In certain embodiments, a target of interest comprises retinal tissue in an eye of a subject.

Presently disclosed methods comprise use of light having a wavelength in a yellow range, light having a wavelength in a red range, light having a wavelength in a near-infrared (NIR) range, or any combination thereof (e.g., any two, or all three of, light having a wavelength in a yellow range, light having a wavelength in a red range, and light having a wavelength in a near-infrared (NIR) range). In some embodiments, PBM therapy according the present disclosure includes light of one or more wavelength between 550 nanometers and 1060 nanometers. In certain embodiments, PBM therapy according the present disclosure includes light of one or more wavelengths between 550 nanometers and 980 nanometers.

In certain embodiments, a wavelength in a yellow range is in a range from 550 nm to 620 nm. In further embodiments, a wavelength in the yellow range is in a range from 560 nm to 610 nm. In still further embodiments, a wavelength in the yellow range is in a range from 570 nm to 600 nm. In particular embodiments, a wavelength in the yellow range is 590 nm±15 nm.

In certain embodiments, a wavelength in a red range is in a range from 620 nm to 750 nm. In further embodiments, a wavelength in the red range is in a range from 630 nm to 740 nm. In further embodiments, a wavelength in the red range is in a range from 640 nm to 730 nm. In still further embodiments, a wavelength in the red range is in a range from 650 nm to 720 nm. In yet further embodiments, a wavelength in the red range is in a range from 660 nm to 710 nm. In particular embodiments, a wavelength in the red range is 670 nm±15 nm.

In certain embodiments, a wavelength in a NIR range is in a range from 750 nm to 950 nm. In further embodiments, a wavelength in the NIR range is in a range from 800 nm to 900 nm. In still further embodiments, a wavelength in the NIR range is in a range from 825 nm to 875 nm. In particular embodiments, a wavelength in the NIR range is 850±15 nm.

Other parameters of PBM therapy according to the present disclosure include, for example: light emission; power density; pulsing or continuous light delivery; length of pulsed light; width of pulsed light; temporal pulse shape(s), duty cycle(s), pulse frequency(ies); irradiance per pulse; beam diameter; sequence and number of exposures to the or more administered PBM lights or wavelengths; duration of a exposure to the one or more administered PBM lights or wavelengths; duration of a treatment session; whether a subject's eye is open or closed during all or part of a treatment; or the like.

For example, in certain embodiments, a PBM light or wavelength may be emitted at an intensity of from about 0.001 mW/cm$^2$ to about 100 mW/cm$^2$ or more; e.g., about 0.001, 0.005, 0.01, 0.05, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200 or more mW/cm$^2$, or any integer or non-integer number therewithin. In embodiments comprising administration of PBM light of multiple wavelengths, two or more of the lights can be administered at the same or at different intensities.

In certain embodiments, for example, a method of the present disclosure comprises two or three of: light comprising a wavelength in the yellow range; light comprising a wavelength in the red range; and light comprising a wavelength in a NIR range, wherein: the light comprising the wavelength in the yellow range is emitted from a source at about 1, 2, 3, 4, 5, 6, 7, 8, 9, 10, 11, 12, 13, 14, 15, 16, 17, 18, 19, 20, 21, 22, 23, 24, or about 25 mW/cm$^2$, or more; the light comprising the wavelength in the red range is emitted from a source at about 1, 2, 3, 4, 5, 6, 7, 8, 9, 10, 15, 20, 25, 30, 35, 40, 45, 50, 55, 60, 65, 70, 75, 80, 85, or about 90 mW/cm2; the light comprising the wavelength in the NIR range is emitted from a source at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more mW/cm$^2$. In particular embodiments, a light comprising a wavelength in the yellow range (e.g., about 590 nm) is emitted from a source at about 5 mW/cm$^2$. In particular embodiments, a light comprising a wavelength in the red range (e.g., about 660 nm) is emitted from a source at about 65 mW/cm$^2$. In particular embodiments, a light comprising a wavelength in the NIR range (e.g., about 850 nm) is emitted from a source at about 8 mW/cm$^2$. In certain embodiments, a method comprises administering a light comprising a wavelength in the yellow range (e.g., about 590 nm), a light comprising a wavelength in the red range (e.g., about 660 nm), and a light comprising a wavelength in the NIR range (e.g., about 850 nm), wherein the light comprising the wavelength in the yellow range is emitted at about 5 mW/cm$^2$, the light comprising the wavelength in the red range is emitted at about 65 mW/cm$^2$, and the light comprising the wavelength in the NIR range is emitted at about 8 mW/cm$^2$. It will be understood that in any of the presently disclosed methods, a light that comprises a PBM wavelength in a particular range (e.g., yellow, red, or near infrared) or comprises a particular PBM wavelength or range (e.g., 590 nm or about 590 nm, 660 nm or about 600 nm, 850 nm or about 850 nm) can be partially, substantially, or entirely composed of light of the PBM wavelength. In other words, a stated PBM wavelength can account for, e.g., about 5%, 10%, 20%, 30%, 40%, 50%, 60%, 70%, 80%, 90%, 91%, 92%, 93%, 94%, 95%, 96%, 97%, 98%, 99%, or more of the light.

In any embodiment comprising use of multiple (i.e., two or more) wavelengths, any two or more of the multiple wavelengths can be emitted or delivered simultaneously, concurrently, or in any sequence, including overlapping and non-overlapping sequences and sequences and sequences wherein a resting period comprising no or no PBM light, or PBM light of a different wavelength, is interspersed between the emission or delivery of the two or more wavelengths.

In any of the embodiments disclosed herein, a PBM light can be delivered in a pulsed fashion, a continuous fashion, or both. Pulsed light can be delivered in any shape, frequency, irradiance, duty cycle, or other parameter appropriate to a treatment. In some embodiments, PBM light is pulsed at a frequency of about 1 Hz to 100 Hz, from about 100 Hz to about 1 kHz, less than 1 Hz, or more than 100 Hz. In embodiments that comprise two or more PBM wavelengths, any two or three wavelengths may be delivered to a subject or subject eye in a pulsed or a continuous fashion. In some embodiments, one of: a wavelength in the yellow range, a wavelength in the red range, and a wavelength in the NIR range are delivered at least in part in a pulsed fashion; and another of a wavelength in the yellow range, a wavelength in the red range, and a wavelength in the NIR range are delivered at least in part in a continuous fashion.

In certain embodiments, a PBM light according to the present disclosure has any beam diameter that is suitable to reach and sufficiently contact a target area (e.g., cell, organ, body party, or tissue). A beam diameter can be measured at a treatment pane, at the point of exit or emission from a light source, or at any point therebetween. Unless otherwise indicated, a diameter of a light beam as described herein refers to the diameter at a treatment plane. Suitable beam diameters and light intensities can be readily determined by a person of ordinary skill in the art in regard to, for example, the particular cell, organ, body part, or tissue to be targeted, the type, severity, and stage of disease or condition, the size, age, eye (iris) color of the subject, the distance from the point of light emission to the target cell, organ, body part, or tissue, or the like. For example, in certain embodiments, a beam for providing PBM light to a retinal tissue in an eye of a subject having or suspected of having dry age-related macular degeneration can be about 10, 15, 20, 30, 35, 40, 45, or more mm in diameter. In particular embodiments, a beam has a diameter of about 30 mm.

Treatment exposure times will also be readily determined by those of ordinary skill in the art with regard to, for example, the particular relevant feature(s) of the subject, the disease or condition to be treated, the type, intensity, and/or wavelength(s) of light being administered, or the like. In some embodiments, a treatment can comprise administering one or more light comprising a PBM wavelength for between about 0.0001 milliseconds and about 1 hour, or more. In certain embodiments, a treatment session comprises administering one or more PBM light, wherein each of the one or more light is administered for about 1, 5, 10, 15, 20, 25, 30, 35, 40, 45, 50, 55, 60, 65, 70, 75, 80, 85, 90, 95, 100, 105, 110, 115, 120, 130, 140, 150, 160, 170, or 180 seconds or more. In some embodiments, a total time of a treatment session comprises the combined durations of the light administration, and can range from less than about one minute to ten or more minutes. In particular embodiments, a treatment session comprises a total treatment (e.g., exposure) time of less than about 20 minutes, less than about 15 minutes, less than about 10 minutes, or less than about 9, 8, 7, 6, 5, 4, 3, or 2 minutes, or less than about one minute. In some embodiments, a treatment session comprises a total treatment (e.g., exposure) time of less than about 5 minutes, or is about 4 minutes. The total treatment time can refer to treatment of a single eye (even if more than one eye of a subject is to receive treatment in the session) or of more than one eye.

In any of the herein described embodiments, a method can comprise a treatment session that includes one or more phases, wherein the one or more phases are each characterized by any one or a combination of the herein described PBM parameters; e.g., light color, light wavelength, pulsed versus continuous light, light intensity, light delivered to an open eye, light delivered to a closed eye through an eyelid, light delivered to a first eye and optionally to a second eye, a resting period wherein no light or no PBM light is being administered or delivered, varying intensities of the light(s), or the like.

For example, in certain embodiments, a method can comprise a first phase comprising administering light (e.g., one or two or more beams) comprising a first and a second PBM wavelength, and a second phase comprising administering light comprising a third wavelength. It will be understood that phases can comprise lights, wavelengths, continuous versus pulsing, rest times, changes in intensity, or the like in any sequence and/or combination. In general, the lights, wavelengths, light intensities, treatment times, phases, beam diameters, pulsing and/or continuous delivery during a treatment session according to the presently disclosed methods will be selected according to their efficacy or potential efficacy for treating the given subject and/or condition, by the convenience and comfort threshold for the subject (e.g., not keeping an eye open for more than few minutes to receive PBM), by safety considerations (e.g., using light of an appropriate intensity for PBM, and avoiding undesirable heating, ablation, cauterization, coagulation, or other forms of damage). Non-limiting examples include all of the PBM treatment parameters, and the specific treatment methods and combinations of the PBM treatment parameters described in PCT Patent Publication No. WO 2016/040534A1, which are incorporated herein by reference.

In specific embodiments, a method comprises administering PBM light for a total treatment time of about 250 seconds, wherein the method comprises: a first phase comprising about 35 seconds wherein pulsed yellow and NIR wavelengths of about 590 nm and about 850 nm, respectively, are delivered to an open eye of a subject with respective maximal light emissions of about 5 mW/cm$^2$ and about 8 mW/cm$^2$; a second phase comprising about 90 seconds wherein a continuous red wavelength of about 660 nm with a maximal emission of about 65 mW/cm$^2$ is administered to (i.e., through) a closed eyelid of the subject; a third phase comprising about 35 seconds wherein pulsed yellow and NIR wavelengths of about 590 nm and about 850 nm, respectively, are delivered to an open eye of a subject with respective maximal light emissions of about 5 mW/cm$^2$ and about 8 mW/cm$^2$; and a fourth phase comprising about 90 seconds wherein a continuous red wavelength of about 660 nm with a maximal emission of about 65 mW/cm$^2$ is administered to (i.e., through) a closed eyelid of the subject. An exemplary embodiment of PBM treatment parameters is provided in Example 1 (Table 2).

PBM Therapy Regimens for Re-Treatment

In any of the presently disclosed methods, PBM can be administered to the subject or eye of the subject one or more times (e.g., sessions) per day, or one or more times per week, month, or year. In some embodiments, a method comprises administering PBM to the subject (or eye of the subject) 1, 2, 3, 4, 5 or more times per week, optionally for 1, 2, 3, 4, 5 or more weeks. In certain exemplary embodiments, a method comprises administering PBM to the subject or subject eye about 3 or 4 times per week for about 3 or 4 weeks. In some embodiments, the subject has previously received PBM according to the same or a similar (or different) regime about 3, 4, 5, 6, or more months previous. Timing between successive administrations of PBM in a treatment regime, regimen, or course of treatment can be determined according to, for example: the nature, state, severity, or progression of the disease or condition; responsiveness of the subject or disease to a prior PBM treatment; one or more subject characteristics including, for example, any of the characteristics described herein (e.g., baseline AREDS score, baseline visual acuity, or the like), the convenience to the subject, or any combination thereof.

For example, in the present disclosure, it was determined that re-treatment with PBM therapy about 4 to 6 months following a prior or initial treatment can help sustain or renew a benefit achieved with the prior or initial treatment. Accordingly, in any of the herein described embodiments, a subject that receives PBM therapy has received PBM during a prior or initial about 4 to 6 months previously. In further embodiments, the subject may be receive a subsequent treatment comprising PBM therapy, for example, about 4 to about 6 months thereafter. By way of illustration, in some embodiments a subject who has received PBM therapy as disclosed herein to treat dry AMD at month 0 receives PBM therapy according to the present methods at about month 4 to about month 6 (e.g., for about 3 or 4 weeks), and thereafter receives PBM therapy at about month 8, about month 10, or about month 12. A treatment schedule according to the present disclosure can continue unaltered, or altered according to any parameter, for months, years, or decades.

Devices

Light suitable for PBM can be produced, for example, by a laser (e.g., a low-power laser) or a non-coherent light source (e.g., a light emitting diode (LED), a laser diode (e.g., a gallium-aluminum-arsenic (GaAlAs) laser diode, an aluminum gallium indium phosphide (AlGaLnP) laser diode, a diode-pumped solid state (DPSS) laser, a vertical cavity surface-emitting laser (VCSEL) diode, or the like), a lamp, or the like).

Any suitable light-emitting device can be used to provide PBM therapy of the present disclosure. It will be understood that PBM light can be generated and/or administered using a single device or source or using different devices or sources during a treatment session or over the course of a treatment regimen (e.g., comprising multiple treatment sessions). Exemplary devices include all of those disclosed in PCT Publication No. WO 2016/040534A1, as well as those comprising combinations of the features disclosed therein, (see also the VALEDA™ Light Delivery System by LumiThera) and U.S. Pat. No. 9,592,404. Other devices include the Warp 10™ (Quantum Devices, Inc.; Barneveld, WI) and the GentleWaves® (Light Bioscience LLC; Virginia Beach, VA) instruments.

In certain embodiments, a device comprises a microprocessor or microcontroller that modulates one or more parameter of PBM therapy; e.g., any one or more of the parameters described herein. In some embodiments, a device is programmable and can, for example, provide a PBM therapy that is customized or tailored for a particular subject, subject eye, or group, class, or category of subjects. Therapeutic settings (e.g., parameters) for providing PBM to a subject can be adjusted during a treatment session (e.g., in real time), or between treatment sessions, or over the course of a treatment regimen, regime, or program based on. Exemplary microprocessors and devices, systems, and methods comprising use of the same for providing PBM therapy are described in PCT Publication No. WO 2016/040534A1, and are incorporated herein.

PBM Based on Patient Criteria

In another aspect, methods are provided for treating dry age-related macular degeneration in a subject that are based, in part, on subject criteria that may indicate an improved likelihood of or capacity for response to PBM to treat the AMD.

Briefly, in the present disclosure, it was determined that in some cases, subjects that benefit most from PBM therapy are those who have better baseline (i.e., pre-treatment) vision and/or who receive PBM at an early stage of the disease. For example, in some embodiments, a method comprises administering PBM therapy to a subject or subject eye that has or is suspected of having dry AMD and (e.g., was selected on the basis of): (i) is categorized as AREDS 1, 2, 3 (e.g., AREDS 3 with drusen only), or 4; (ii) has a pre-treatment best corrected visual acuity (BCVA) letter score of about 70, 71, 72, 73, 74, 75, 76, 77, 78, 79, 80, or more; (iii) does not have geographic atrophy (GA) with central foveolar involvement; (iv) has a Snellen BCVA equivalent score of 20/100 or better; or (v) any combination of (i)-(iii). Classification of a subject has having any one or more of the criteria provided in (i)-(v) can be readily determined by a person of ordinary skill in the art, e.g., an ophthalmologist. Without being bound by theory, earlier intervention with PBM according to the present disclosure may have a greater therapeutic effect due to the greater amount and/or improved state of health of tissue and cells that can be stimulated by the PBM, whereon the stimulated cells or tissue can act to remove or slow the spread, accumulation, or production of toxic substances (e.g., drusen), repair or remove diseased cells, or the like. In some embodiments, a subject eye has a pre-treatment AREDS classification of AREDS 1. In some embodiments, a subject eye has a pre-treatment AREDS classification of AREDS 2. In some embodiments, a subject eye has a pre-treatment AREDS classification of AREDS 3. In some embodiments, a subject eye has a pre-treatment AREDS classification of AREDS 4.

In any of the embodiments of this aspect, any PBM parameter(s) or treatment schedules or regimes, including any combination of those described herein (and those incorporated by reference or otherwise known to those of ordinary skill in the art), can be used to treat the subject (or subject eye). In some embodiments, a subject selected or identified according to the present criteria receives re-treatment as disclosed herein; e.g., a subject selected for or identified as having any one or more of the present selection criteria is administered PBM therapy and has received a prior or initial PBM therapy, and may, in some embodiments, receive further PBM treatment. In certain embodiments of any of the herein described methods, the timing and/or type of a treatment method relative to a prior treatment (or the decision as to when to administer a subsequent treatment) can be determined according to the type and degree of response achieved by the subject (or subject eye) to treatment.

By way of illustration, as shown in the Examples, subjects who received PBM therapy for 3-4 weeks and shortly thereafter (i.e., at month 1) achieved an increase in BCVA score of 5 or more letters relative to pre-treatment baseline, which benefit was generally maintained until about month 6, whereupon re-treatment with PBM rescued the benefit. Accordingly, in certain embodiments, a subject receiving PBM at about 4 to 6 months after a prior or initial PBM therapy session is a subject who achieved an increase of in BCVA score of 5 or more letters (e.g., at 1 month after beginning PBM, and relative to baseline BCBA) after the prior or initial PBM therapy. In certain embodiments, a subject who has received prior PBM and had an increase in BVCA score of 5 or less at one month after beginning the prior BPM may receive re-treatment at about 1 to about 3 months after the prior or initial PBM therapy, which re-treatment can comprise the same PBM parameters as the prior or initial therapy, or may differ in one or more parameters (e.g., longer treatment times, greater intensity of delivered PBM light, more or more frequent administrations of PBM during the course of the re-treatment regime, or the like).

EXAMPLES

Example 1

Clinical Study of PBM Therapy for Dry Age-Related Macular Degeneration

Study Design and Enrollment Criteria

A single-center prospective, sham-controlled, double-masked pilot clinical study was conducted using PBM to treat patients with a clinical diagnosis of dry AMD. A total of forty (40) subjects were screened, of which thirty (12 male, 18 female) subjects aged 50 or older and presenting with a clinical diagnosis of dry AMD were enrolled in the study. The mean age for subjects was 76 (±8.3) years with a range between 52 years of age and 90 years of age. The median age was 74. Subjects' eyes were only accepted into the study if they were independently diagnosed with dry AMD (median duration of 7.8 years (±7.6) since diagnosis) and categorized as AREDS 2, 3 or 4 by an OCT for dry AMD and had BVCA scores as determined by the Early Treatment Diabetic Retinopathy Study (ETDRS) Visual Acuity chart with a letter score between 50 and 85 (Snellen equivalent from 20/40 to 20/200). An independent, masked imaging expert reviewed OCT and FAF images to determine dry AMD etiology and confirm inclusion/exclusion criterion. Subjects were excluded if they had cognitive impairment or if their eyes exhibited neovascular maculopathy (previous or active wet AMD), a history of epilepsy, media opacification, received past invasive ocular surgery, or had any other significant ocular disease.

Both eyes were included if inclusion criteria were met in both eyes. Therefore, an adapted AREDS classification was used, as each eye was individually assessed for the presence of center involving GA. Thus, the fellow eye was not automatically deemed AREDS category 4 if the other eye showed center involving GA.

Characteristics of Enrolled Patients Eyes

Figure 2:
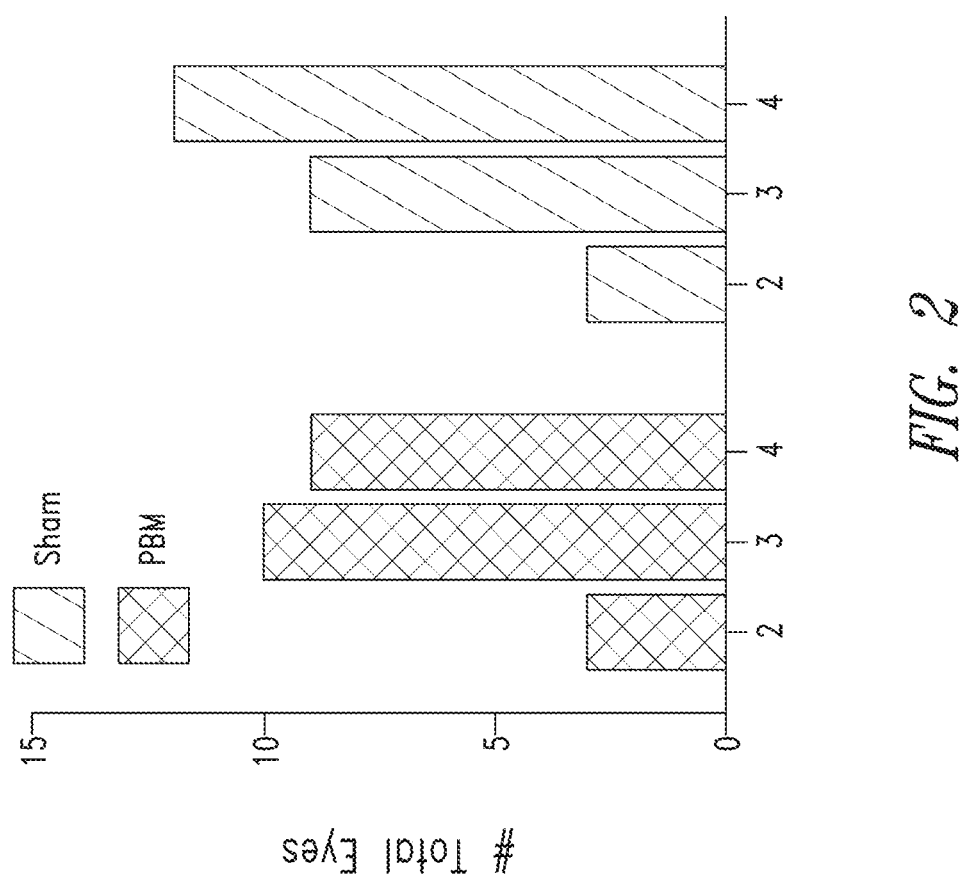
FIG. 2 shows the number of total patient eyes in the present clinical study that received PBM treatment or a sham treatment and Age Related Eye Disease Study (AREDS) category 2, 3, or 4 classification.

A total of 46 eyes were qualified and randomized at a 1:1 ratio into two groups: Sham treatment (S-1); and PBM Treatment (T-2). The study enrolled a total of one subject in AREDS category 2, 17 subjects in AREDS category 3 and 28 subjects in AREDS category 4. The PBM treatment group's baseline mean VA letter score was 74. The number of eyes per AREDS and treatment group is shown in FIG. 2 and Table 1, below. Table 1 also reports baseline disease distribution.

TABLE 1

Baseline Disease Distribution According to AREDS Classification and Study Variables

| | Number of Subjects (n, %) | |
|---|---|---|
| | Sham (n = 22 eyes) | PBM (n = 24 eyes) |
| Adapted AREDS Classification | | |
| AREDS Category 2 | 0, 0.0% | 1, 4.2% |
| AREDS Category 3 | 5, 22.7% | 9, 37.5% |
| AREDS Category 4 | 17, 77.3% | 14, 58.3% |
| GA | 18, 81.8% | 16, 66.7% |
| RPD | 14, 63.6% | 13, 54.2% |
| Baseline Study Variable (units) | | |
| Foveola Involvement | 9, 40.9% | 11, 45.8% |
| ORA | 2, 9.0% | 5, 20.8% |
| iRORA | 0, 0.0% | 5, 20.8% |
| Refractile drusen | 4, 18.2% | 12, 50.0% |
| PR Intact | 0, 0.0% | 2, 8.3% |
| Mean CRT (µm) | 210.7 ± 78.7 | 241.5 ± 58.6 |
| Mean RV (mm$^3$) | 7.8 ± 0.9 | 8.2 ± 0.7 |
| Mean GA size (mm$^2$) | 7.5 ± 7.8 | 6.0 ± 5.7 |
| End of Study Variable (units) | | |
| ORA | 2, 0.9% | 4, 16.7% |
| iRORA | 0, 0.0% | 4, 16.7% |
| PR Intact | 0, 0.0% | 2, 8.3% |
| Mean CRT (µm) | 209.9 ± 91.4 | 229.4 ± 61.5 |
| Mean RV (mm$^3$) | 7.7 ± 1.1 | 8.0 ± 0.8 |
| Mean GA size (mm$^2$) | 7.8 ± 7.8 | 6.5 ± 6.4 |

GA, geographic atrophy; RPD, reticular pseudodrusen; SD, standard deviation; ORA, outer retinal atrophy; iRORA, incomplete retinal pigment and outer retinal atrophy; PR, photoreceptor; CRT, central retinal thickness; RV, retinal volume.

The majority of subjects had intermediate to advanced stage dry AMD as categorized by high prevalence of subjects with AREDS categories 3 (30.4%) and 4 (67.4%). The majority of eyes had GA (73.9%). In the Sham group, 52.9% of eyes that were categorized as AREDS category 4 with central 1.0 mm involving GA also had foveola involvement. In the PBM group, 78.5% of eyes that were categorized as AREDS 4 with central 1.0 mm involving GA also had central foveola involvement. No statistical differences between the Sham and PBM treatment groups were seen in the distribution of AREDS categories (Fisher's Exact Test, p=0.27). In total, almost half (20/46 eyes, 43.5%) of all eyes in this study were categorized as AREDS 4 with foveola involving GA.

Treatments

Subjects in the T-2 group were treated with the LumiThera multi-wavelength Valeda™ Light Delivery System emitting a multi-wavelength LED treatment comprised of 590, 670 and 850 nm wavelengths (yellow, red, and near infrared ranges, respectively). The treatment parameters and specifications are shown in Table 2.

TABLE 2

PBM Treatment Parameters

| Parameter | Specification(s) |
|---|---|
| Light sources | Light Emitting Diodes (LEDs) |
| Light emission (maximal) | 590 nm output: 5 mW/cm$^2$ |
| | 660 nm output: 65 mW/cm$^2$ |
| | 850 nm output: 8 mW/cm$^2$ |
| Beam diameter | 30 mm (nominal) at treatment plane |
| Treatment exposure time | A total of 250 seconds (4 minutes 10 seconds). There are 4 phases: |
| | 1: 35 seconds, patient's eyes open [Pulsed yellow and NIR wavelengths] |
| | 2: 90 seconds, patient's eyes closed [Continuous red wavelength] |
| | 3: 35 seconds, patient's eyes open [Pulsed yellow and NIR wavelengths] |
| | 4: 90 seconds, patient's eyes closed [Continuous red wavelength] |

The sham treatment that emitted an approximate 100× reduction in treatment dose (590 and 670 nm) was utilized for the S-1 group. The 850 nm (NIR) wavelength was not provided in the Sham treatment.

Subjects received nine Sham or PBM treatment sessions (approx. 3×/week) after the screening visit, beginning at baseline, during a 3-4 week period followed by follow-up visits at months 2 and 3. Subjects were retreated at 6 months for another nine treatment sessions and followed to month 12, with a follow-up visit at month 9. Subjects could use AREDS vitamin supplementation, however no change in supplements one month prior to the study and during the study trial were allowed. At months 1, 2, 3, 6, 7, and 12, subjects were tested for clinical (visual acuity, VA; contrast sensitivity, CS), quality of life (Visual Function Questionnaire-25, VFQ25) and anatomical (optical coherence tomography, OCT; Fundus Autofluorescence, FAF; microperimetry (RS)) outcomes. Interim analysis was conducted on data collected during the first three months of the study, and included data collected from screening, baseline, day 18 (final treatment day), and follow up visits (Month 2 and 3 assessments). Final analysis was conducted on data collected at the 1, 3, 5, 7, and 12-month marks. Data was restricted to group treatment results and individual treatment assignments remained masked until study completion.

Change from baseline was used as the preferred outcome metric and a linear mixed effects model by ranks was used for the statistical analysis. Some subjects missed follow-up visits at 2 and 3 months. Statistical analyses were performed using R version 3.0 or higher (R: The R Project for Statistical Computing; https://www.r-project.org/). Linear mixed effects analyses were performed using the R package NLME. Graphs were generated using the R package ggplot2. CS, BVCA, and microperimetry analyses (Examples 2, 3, and 4, respectively) used a linear mixed effects (LME) model for comparisons. Changes pre- and post-PBM within the PBM group and pre and post-sham within the sham group were analyzed using a Wilcoxon signed rank test for paired data (significance set at p<0.05). A Wilcoxon rank sum (Mann-Whitney U) test was used to compare the difference between PBM-treated and sham-treated subjects in changes at selected intervals. VFQ-25 analysis (Example 6) used a linear regression model. A Fisher's Exact Test was used to analyze AREDS category distribution between treatment groups. Two-sided p-values less than 0.05 were considered statistically significant.

Two subjects withdrew consent. One subject withdrew after the first round of treatment was completed; one due to an inability to travel to the study site, the other having completed all treatments but missing the month 3 follow-up visit.

A total of 17 adverse events (AEs) were reported by the 3-month mark. All ocular AEs were minor or moderate in intensity and no AEs were related to the device. A total of 5 AEs were reported in the Sham group and 16 AEs in the Treatment group (Table 3). Subjects and study staff were masked to the treatment. The study was conducted in compliance with the protocol, Good Clinical Practice (GCP) guidelines, Health Canada regulatory requirements and all other applicable regulatory requirements. The study was performed in adherence to the guidelines of the Declaration of Helsinki.

Example 2

Re-Treating with PBM Therapy Maintains Improvement in Contrast Sensitivity in Dry AMD Patients The Functional Acuity Contrast Test (FACT, Stereo Vision Optec 6500, USA) was performed at 1.5, 3, 6, 12 and 18 cycles per degree (CPD) prior to and following treatment to provide an assessment of contrast sensitivity at a range of functionally significant spatial frequencies. FACT consists of five rows of nine grating patches. The rows increase in spatial frequency from A through E, A being the low, B and C, middle and D and E, the high spatial frequencies. CS data from the FACT tests are summarized in Table 3.

TABLE 3

Summary of Constrast Sensitivity Data (FACT)

| Comparison | # Eyes | Group | P-value | Mean Change |
|---|---|---|---|---|
| BL vs. M1 | 24 | PBM | 0.003* | 0.35 |
| BL vs. M1 | 22 | Sham | 0.184 | 0.09 |
| BL vs. M6 | 23 | PBM | 0.032* | 0.30 |
| BL vs. M6 | 21 | Sham | 0.831 | −0.04 |
| BL vs. M7 | 23 | PBM | 0.043* | 0.31 |
| BL vs. M7 | 21 | Sham | 0.378 | 0.05 |
| BL vs. M12 | 23 | PBM | 0.026* | 0.31 |
| BL vs. M12 | 20 | Sham | 0.663 | 0.01 |

Figure 3A:
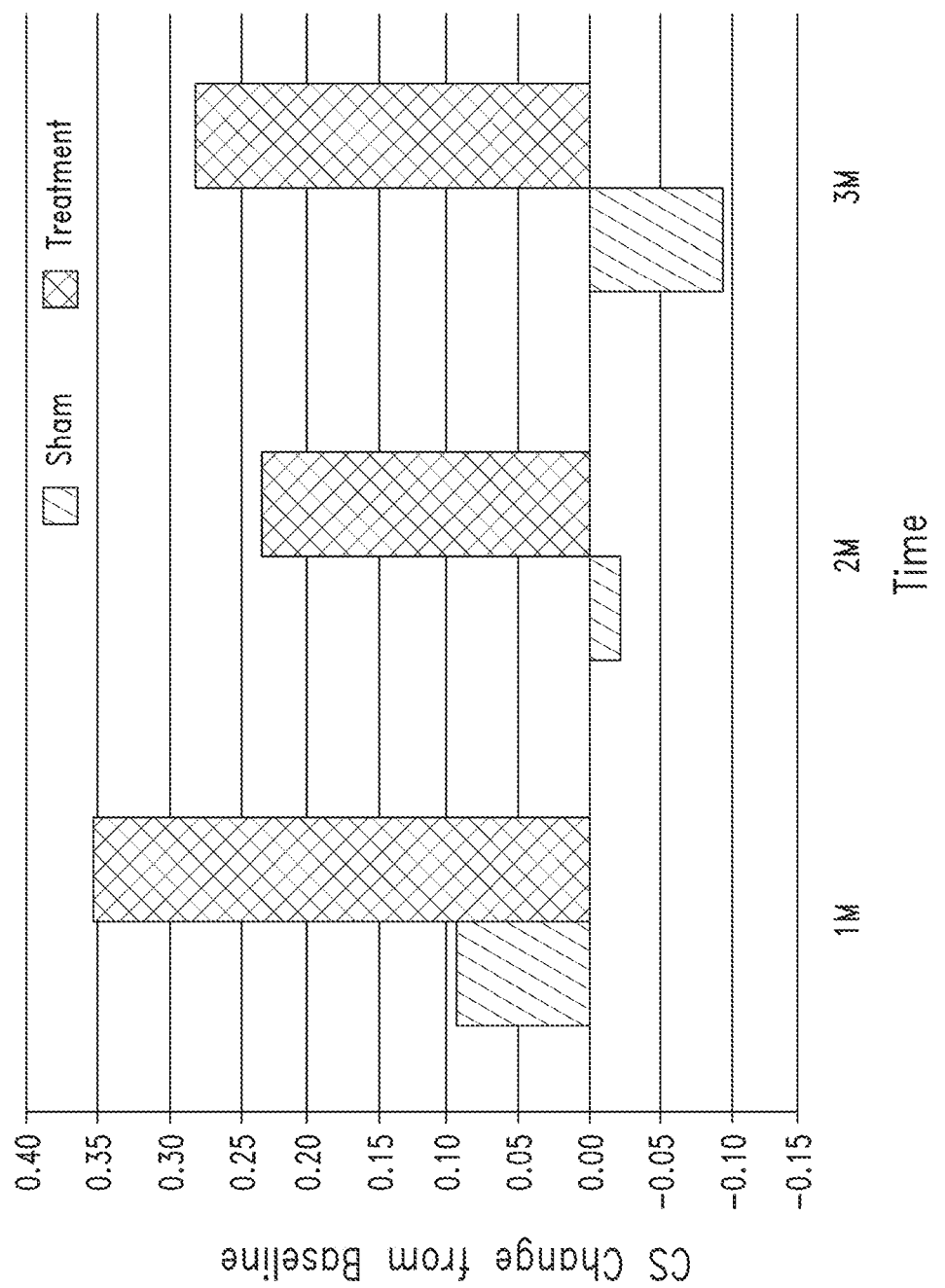
FIGS. 3A-3C show changes in contrast sensitivity (CS) from baseline (i.e., pre-treatment) level for patient eye groups receiving PBM therapy according to the present disclosure or the sham treatment. CS measurements were taken at 1, 2, 3, 6, 7, and 12 months. (3A) Data from M1, M2, and M3 representing eyes with a baseline CS level of E (highest spatial frequency category) as determined using the Functional Acuity Contrast Test (FACT). (3B) Changes in eyes with a baseline CS level of D (second-highest spatial frequency category) as determined using FACT. (3C) CS changes in patient eyes (baseline CS level of E) at M1, M6, M7, and M12 of the trial.
Figure 3B:
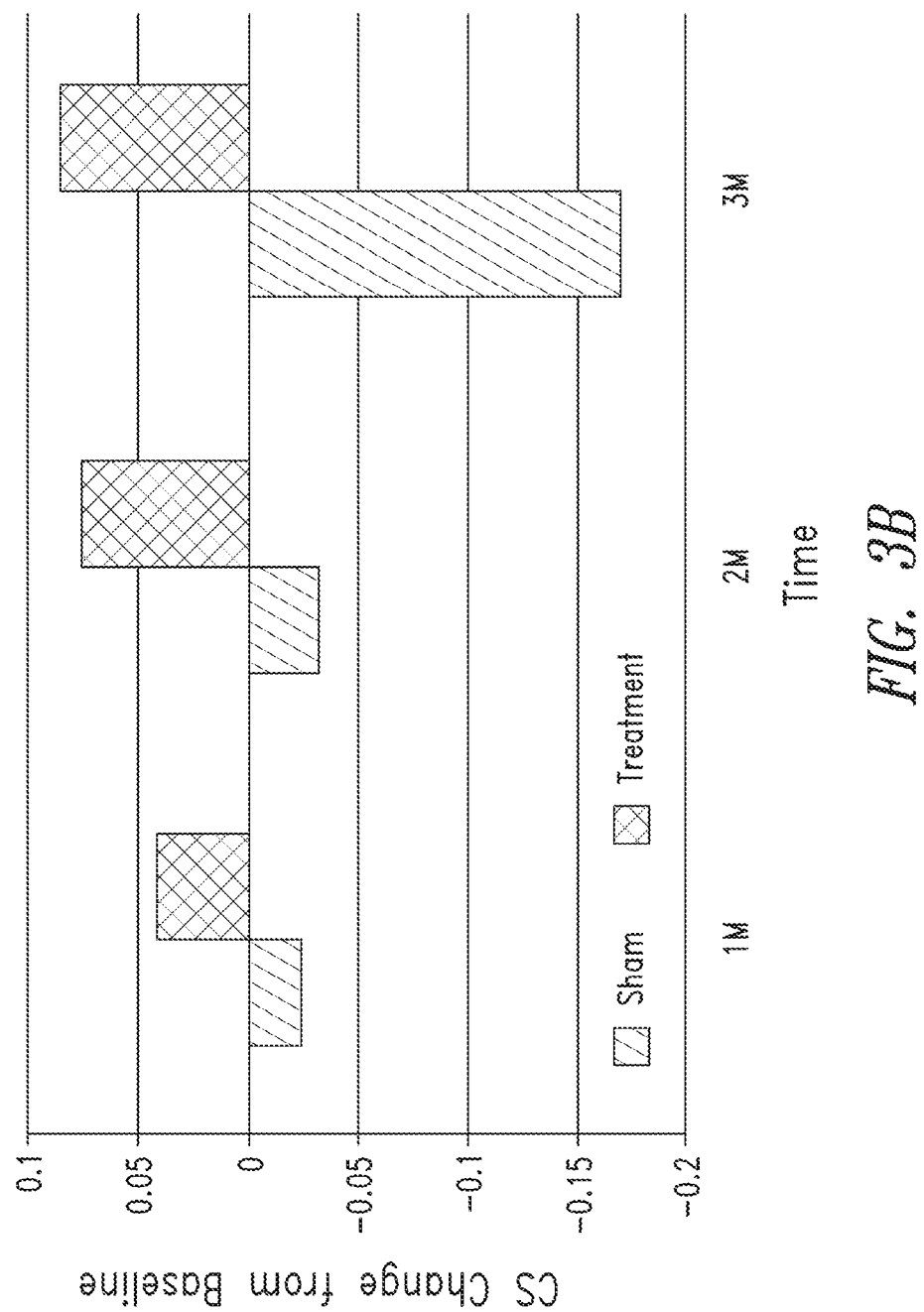
Figure 3C:
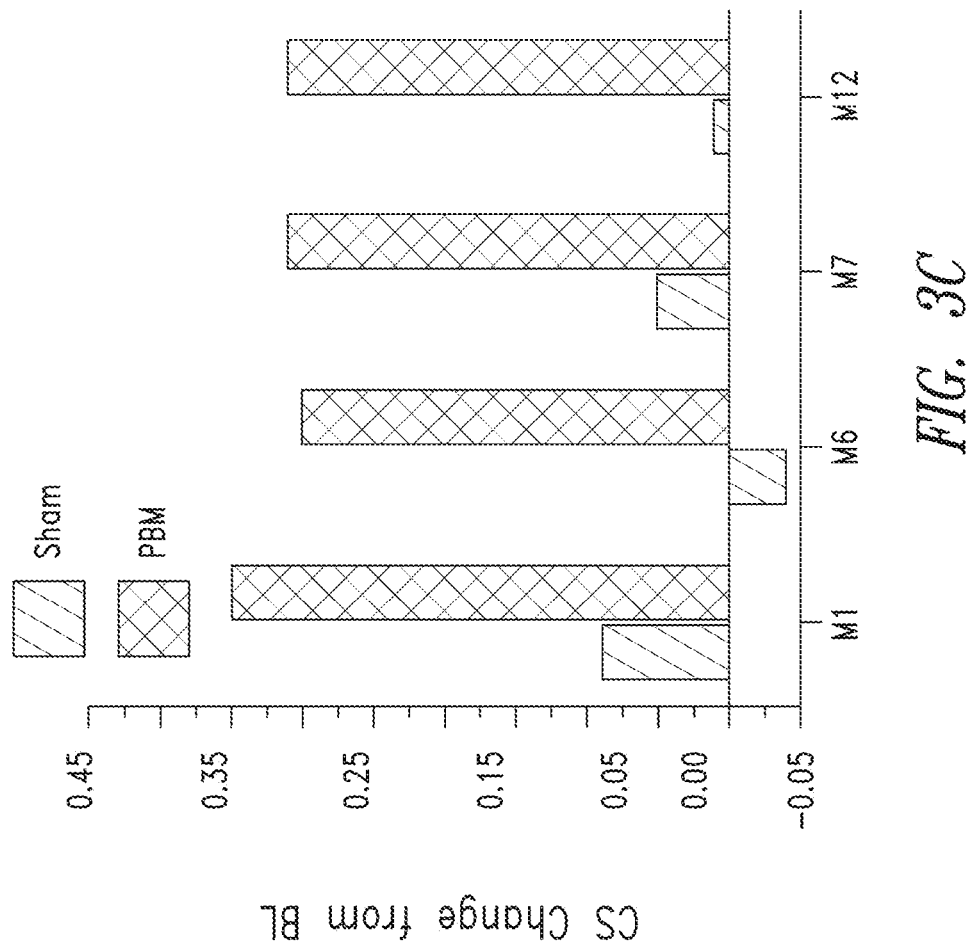

Vision improvements were seen in the CS outcomes at high spatial frequencies (D and E) for out to 12M (FIGS. 3A-3C). A clinically relevant and statistically significant improvement of 0.2-0.3 log units was seen in Level E (18 CDP) change from baseline in the PBM treatment group compared to the sham control at 3, 6, 7, and 12M, (p<0.05; Wilcoxon signed rank test). The increase in CS at M1 was 0.35+0.1 and was maintained (0.30+0.11) at M12. Improvements at 6M were slightly reduced as compared to 1M, and re-treatment at 6M appeared to correlate with increased CS improvement as measured at M7 and M12 (FIG. 3C).

The Level D (12 cycles/degree) CS data for the PBM-treated group showed a positive trend in benefits over the first 6 months from BL but the results were not statistically significant (Wilcoxon signed rank, p=0.45). The level B (3 cycles/degree) CS was significant at 12 months between the PBM-treated and sham groups, p=0.026, but not significant at any other time point. Levels A (1.5 cycles/degree) and C (6 cycles/degree) CS data for the PBM-treated group versus sham-treated group were not statistically significant (Wilcoxon signed rank, p>0.05).

A positive trend in CS was also seen in Level D (12 CPD) CS data over the first 6 months from BL in the PBM treatment from the sham control, but did not reach statistical significance (Wilcoxon signed rank, p=0.45; FIG. 3C). The level B (3 CPD) CS was significant at 12 months between the PBM-treated and sham groups (Wilcoxon signed rank, p=0.026) but not significant at any other time point. Levels A (1.5 CPD) and C (6 CPD) CS data for the PBM-treated group versus sham-treated group were not statistically significant (Wilcoxon signed rank, p>0.05).

The cumulative beneficial results from the CS outcomes translate to a 5-8 letter improvement when converting these CS benefits to VA letter improvements, and CS improvements are consistent with the results seen in VA.

Example 3

Re-Treating with PBM Therapy Maintains Improvement in Visual Acuity in Dry AMD Patients Subjects were assessed for BCVA using the ETDRS charts (Precision Vision, USA) and CS at 1.5, 3, 6, 12 and 18 cycles per degree (Levels A-E) (FACT, Stereo Vision Optec 6500, USA) prior to and following treatment. Sham and PBM-treated subjects had similar baseline BCVA mean letter scores (Sham, 71.9+2.5; PBM, 73.8+1.9).

Figure 4A:
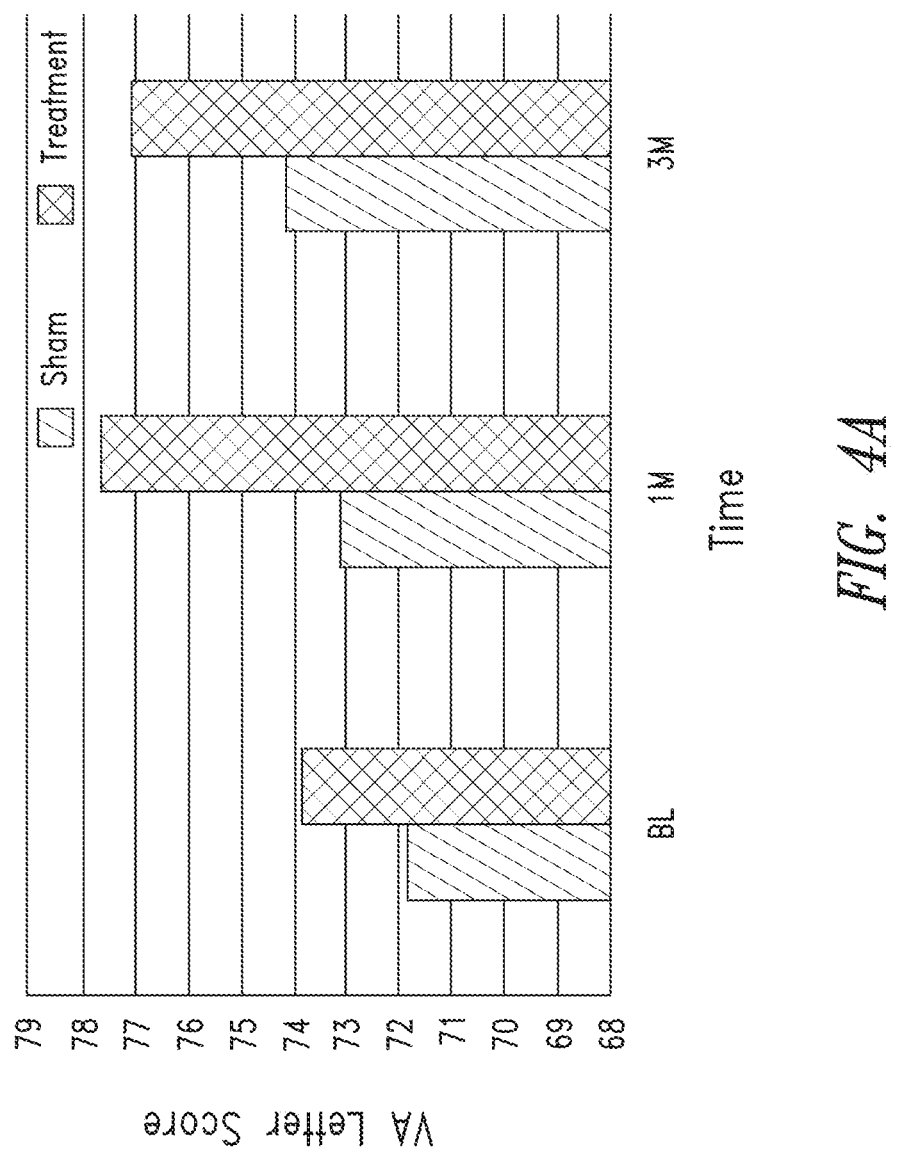
FIGS. 4A and 4B show visual acuity (VA) letter scores over time for patient eyes that received either PBM therapy or the sham treatment. (4A) VA letter scores at BL and after months 1 and 3 of the trial. (4B) VA letter scores at BL and at M1, M6, M7, and M12.
Figure 4B:
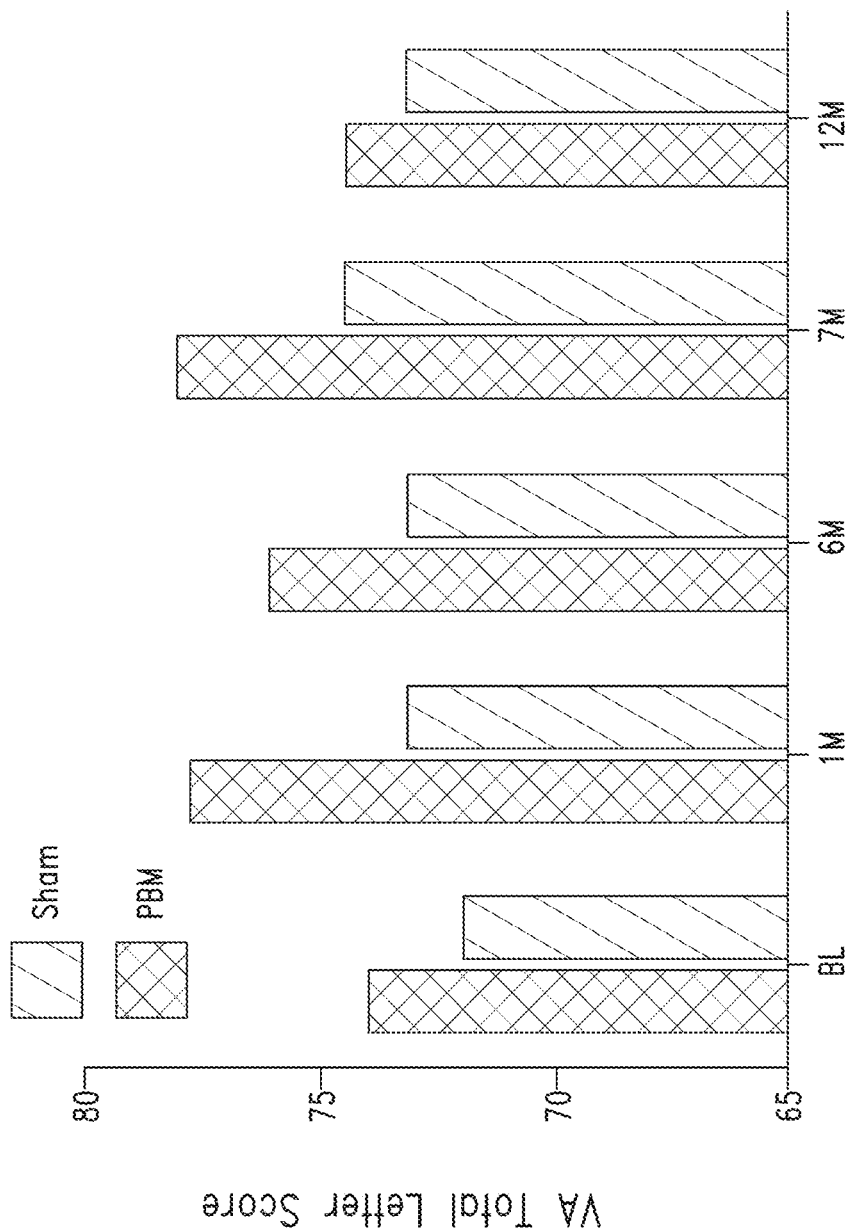

Following the initial treatment series at M1, sham subjects showed no significant change from BL with a one-letter improvement (FIG. 4A), whereas PBM-treated subjects showed an increase in BCVA of ~4 letters to 77.7+2.5 letters. PBM treatment effects on BCVA appeared to start to diminish at the M6 time point (76.1±2.3 letters) just prior to retreatment. Following the second series of PBM treatments at M7, PBM-treated subjects mean BCVA improved to a letter score of 78±2.4. The PBM benefits diminished again by M12 and returned to approximate pre-study BL BCVA levels (74.2±2.6 letters). Overall, the largest benefits were observed at months 1 and 7, immediately following treatment (or re-treatment) (Wilcoxon signed rank; p<0.05) (FIGS. 4A and 4B).

Figure 5A:
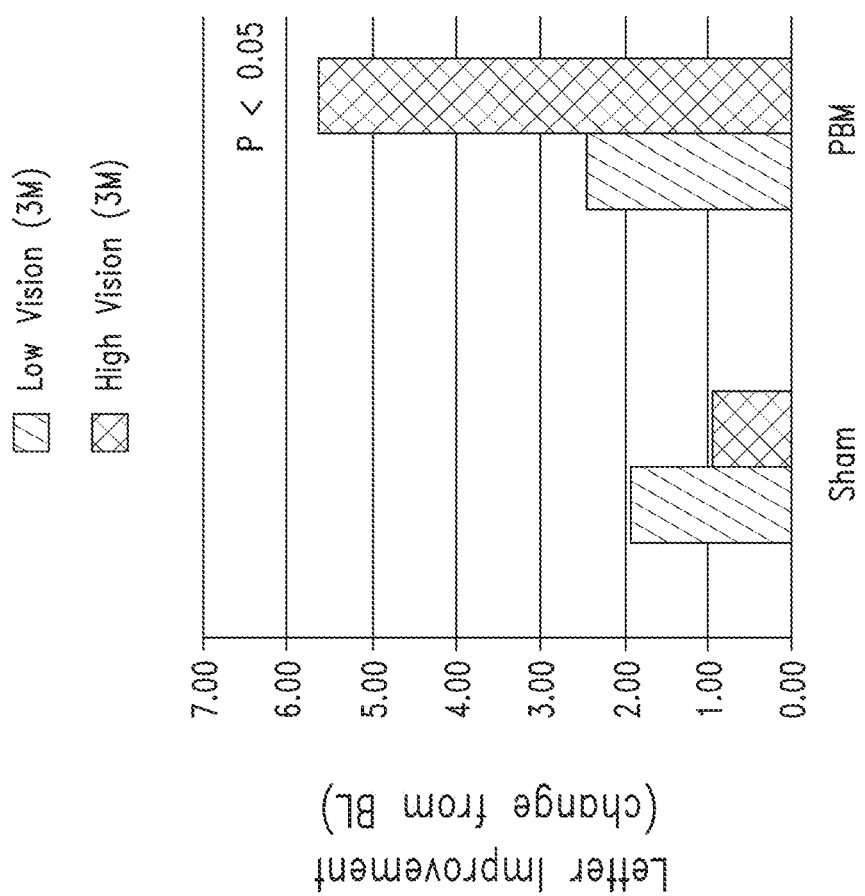
FIGS. 5A and 5B show improvement in VA letter scores over BL of patient eyes that received either PBM therapy or the sham treatment and were classified as having baseline "high vision" (above the patient group mean BL VA score of 74) or "low vision" (below the group mean BL VA score of 74). (5A) Scoring at M3 of the trial. (5B) Scoring at M1, M3, M7, and M12.
Figure 5B:
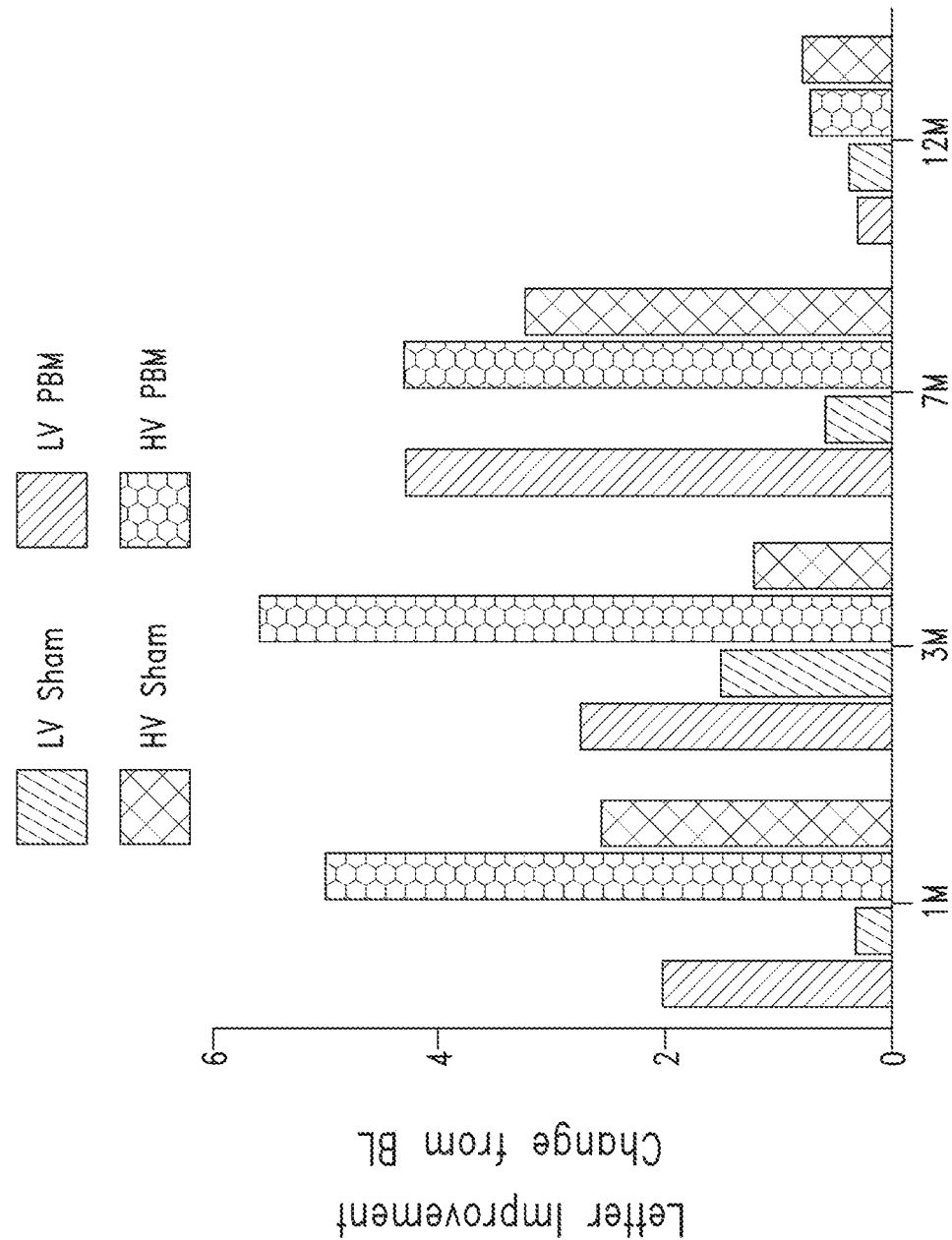

High variability of BCVA changes across subjects supported additional analysis to further understand the subjects' individual responses. Subjects were stratified into either high or low vision groups depending on whether their BL vision was above or below the median BL VA score 76.5. Improvements were seen up to 3 months following treatment in both the high and low vision subjects (FIG. 5A), with much greater gains (≥5 and up to 8 letters; p<0.01) in the high vision group. Gains were also shown at 7 and 12 months, but decreased by 12 months.

Subsequent stratified analysis of the benefits of PBM treatment demonstrated that 50% of PBM-treated subjects showed improvement of 5 or more letters (one-line improvement or better, FIG. 5C) compared to only 13.6% of sham-treated subjects at M1. PBM-treated subjects were evaluated as either low responders (LR) (<5 letters at M1) or high responders (HR) (≥5 letters at M1) to determine the duration of benefit and if PBM treatment benefits were associated with stage of disease. At each visit, within each group (high and low responders) a paired t-test and Wilcoxon signed rank test of BCVA change from baseline was performed. For the course of 1 year, statistically significant benefits (p<0.05) were seen for the HR group at M1, M2, M3, M7 and M9 (but not at visits M6 and M12), which were immediately prior to retreatment and at the conclusion of the study at 12 months. The HR mean BCVA benefit immediately following PBM was 8.0 letters at M1 and 6.0 letters at M7 from BL. The LR group did not show any significant benefits over the course of the study.

These two groups were then analyzed for AREDS stage and for foveola involving GA. Approximately 91.3% of HR subjects were either AREDS category 3 with drusen only or non-central 1 mm involving GA or AREDS category 4 with GA, involving the central 1 mm, but still sparing the foveola. In contrast, the LR subjects were primarily AREDS category 4 (11 of 12), wherein 83.3% (10 of 12) had foveola involving GA.

PBM-treated subjects were further stratified by their BCVA-equivalent Snellen score at BL. Three different groups were created and compared. Subjects with Snellen equivalent scores of 20/200 (ETDRS BCVA letter score of 50) or greater, Snellen 20/100 (ETDRS BCVA letter score of 65) or greater and Snellen 20/80 set (ETDRS BCVA letter score of 70) or greater. The goal was to further define the treatment response in the different patient groups and to optimize inclusion/exclusion criteria for the future clinical studies by evaluating high and low responders by BL vision measurements. Of the LR subjects, 41.7% were eliminated from the study population when the Snellen cut off was reduced to 20/100. The LR subjects were further reduced to 50% when the Snellen cutoff was further reduced to 20/80. The HR population was only reduced to 91.7% at 20/80. The Snellen population comparison suggests that subjects who most significantly respond to PBM treatment are those with remaining good baseline vision at a Snellen equivalents of 20/100 or better.

Example 4

PBM Therapy Improves Retinal Sensitivity in Dry AMD Patients

Retinal Sensitivity was recorded using microperimetry C10-2 grid with 68 tested points (MAIA, Centervue, USA). No statistically significant reduction in Bicurve Ellipse Area Measure (BCEA) fixation stability (FS) was observed between PBM- or sham-treated subjects, LME model analysis (p>0.05) at M1 or M12. However, the BL FS levels were higher in the PBM-treatment group and an improvement in FS following PBM at M1 was seen from 4.4±1.6 to 2.6±0.6 degrees$^2$ in the PBM-treatment group. Subsequently, FS values increased in both the sham-treatment and PBM-treatment group over time to reach levels of 4-6 prior to retreatment at M6. For the PBM group, FS at M6 was 6.5±4.0. Following the PBM retreatment at M7, the FS values again improved to a mean of 2.3±0.7 degrees$^2$, whereas the sham-treatment group did not respond (LME, p=0.0041).

Example 5

PBM Therapy Reduces Drusen Volume and Thickness

All subjects were assessed with 20×20 high speed SD-OCT volume scans (Spectralis OCT, Heidelberg Engineering, Heidelberg, Germany) consisting of 49 section scans each (118 μm distance between each scan, 9 frames averaged) and with 2 central (one horizontal, one vertical) 30 line scans 36 times averaged at baseline and at selected visits for anatomical changes. Fundus autofluorescence imaging (FAF) with 488 nm wavelength (Spectralis OCT, Heidelberg Engineering, Heidelberg, Germany) was performed at the same visits. Subsequent SD-OCT scans were performed using the TruTrack™ follow-up function to allow exact comparison of retina and drusen volume.

SD-OCTs and FAF were analyzed for following parameters: aligned mean central retinal thickness (CRT), aligned mean retinal volume (RV), geographic atrophy (GA) lesion area and aligned drusen volume. The presence of reticular pseudodrusen (RPD), refractile drusen, incomplete and complete outer retinal atrophy (iORA and cORA), incomplete and complete RPE and outer retinal atrophy (iRORA and cRORA[corresponds to GA]), evidence of a CNV, (pseudo) vitelliform lesions and irregularity/disruption of the external limiting membrane (ELM), ellipsoid zone (EZ) and interdigitation zone (IZ) were assessed based on a predefined grading protocol. Sadda et al., *Ophthalmology* 125(4):537-548 (2018).

Figure 6A:
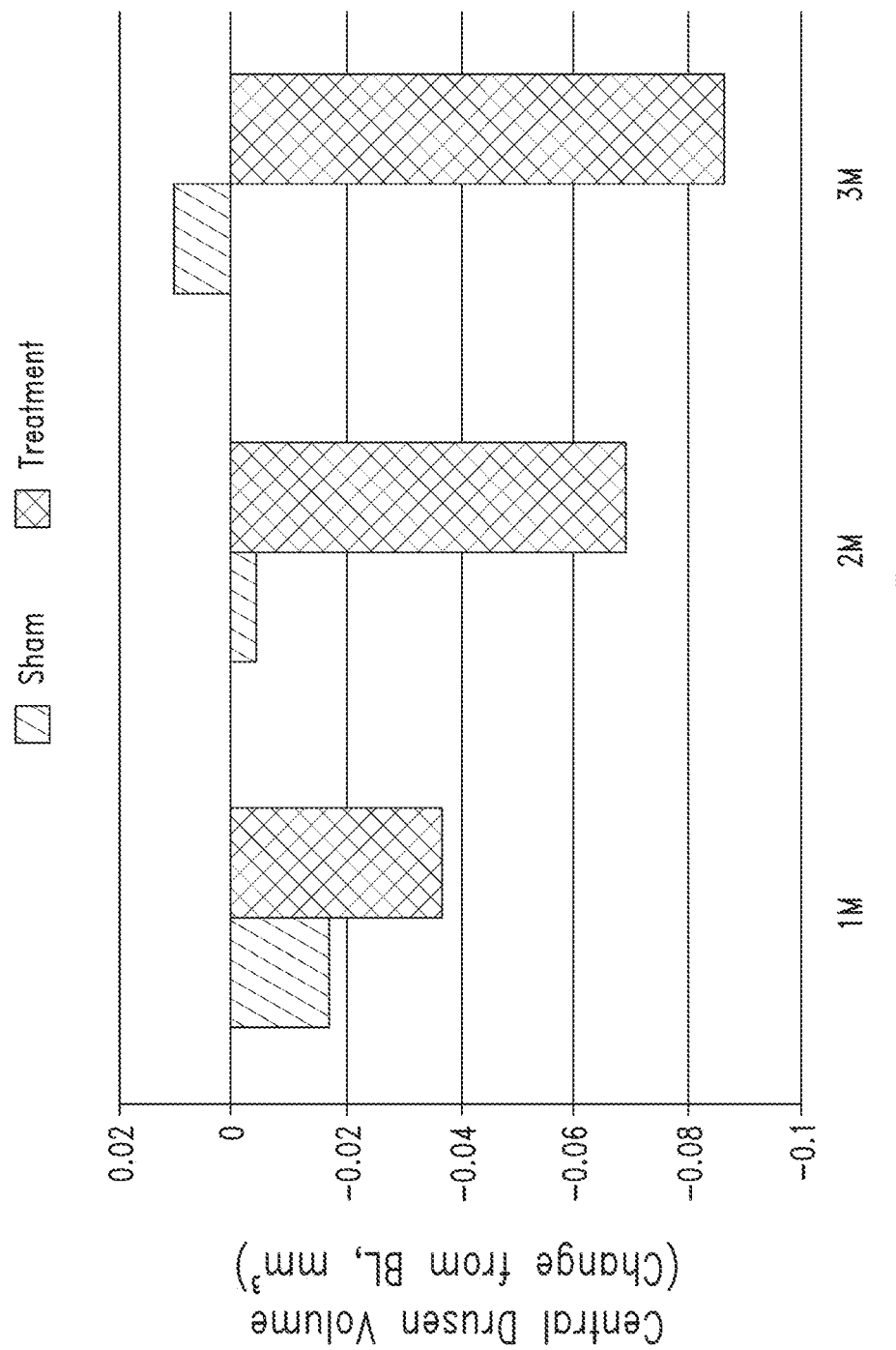
FIGS. 6A-6C show changes in central drusen volume ($mm^3$; 6A, 6C) and thickness (micrometers, 6B) from BL in the patient groups.
Figure 6B:
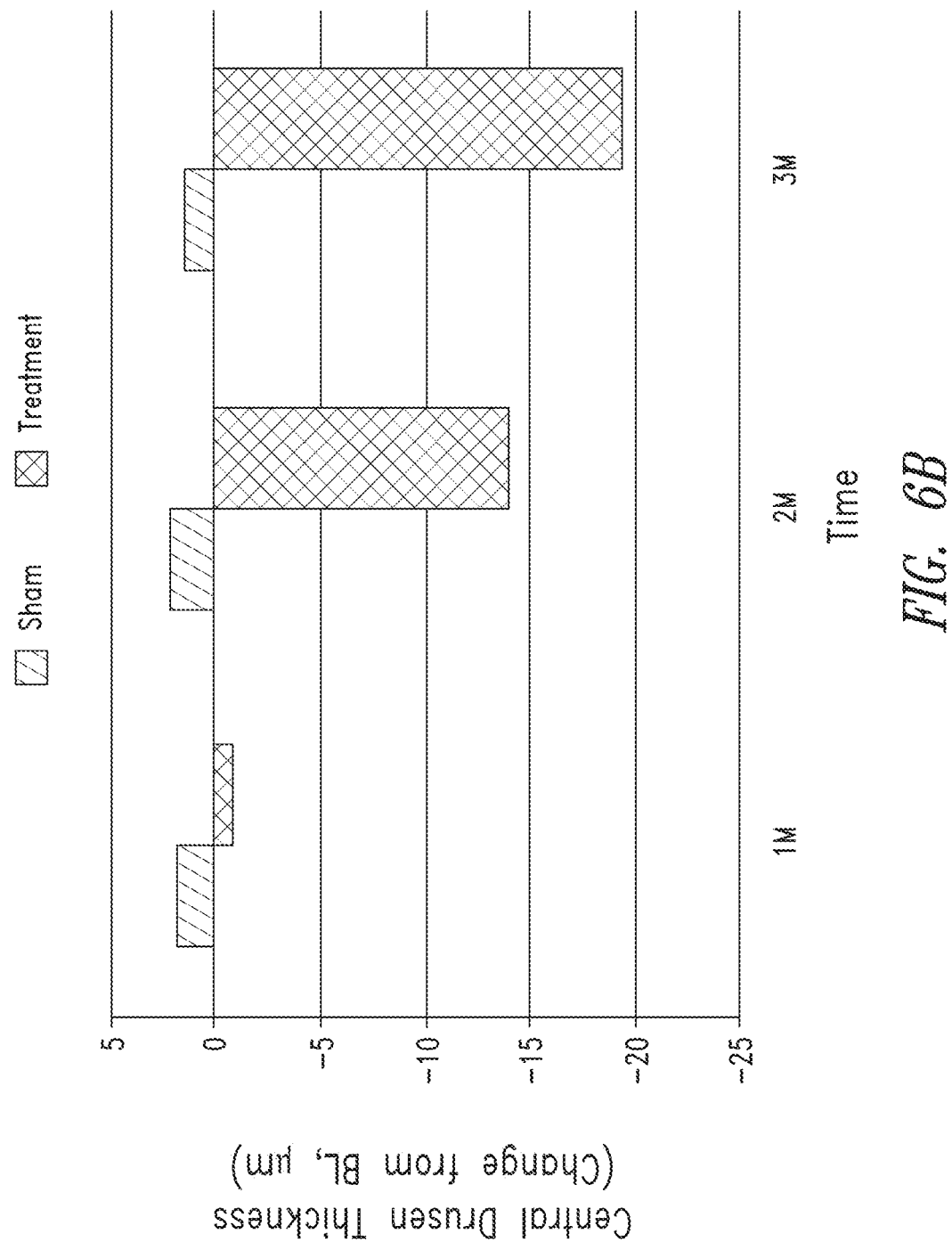
Figure 6C:
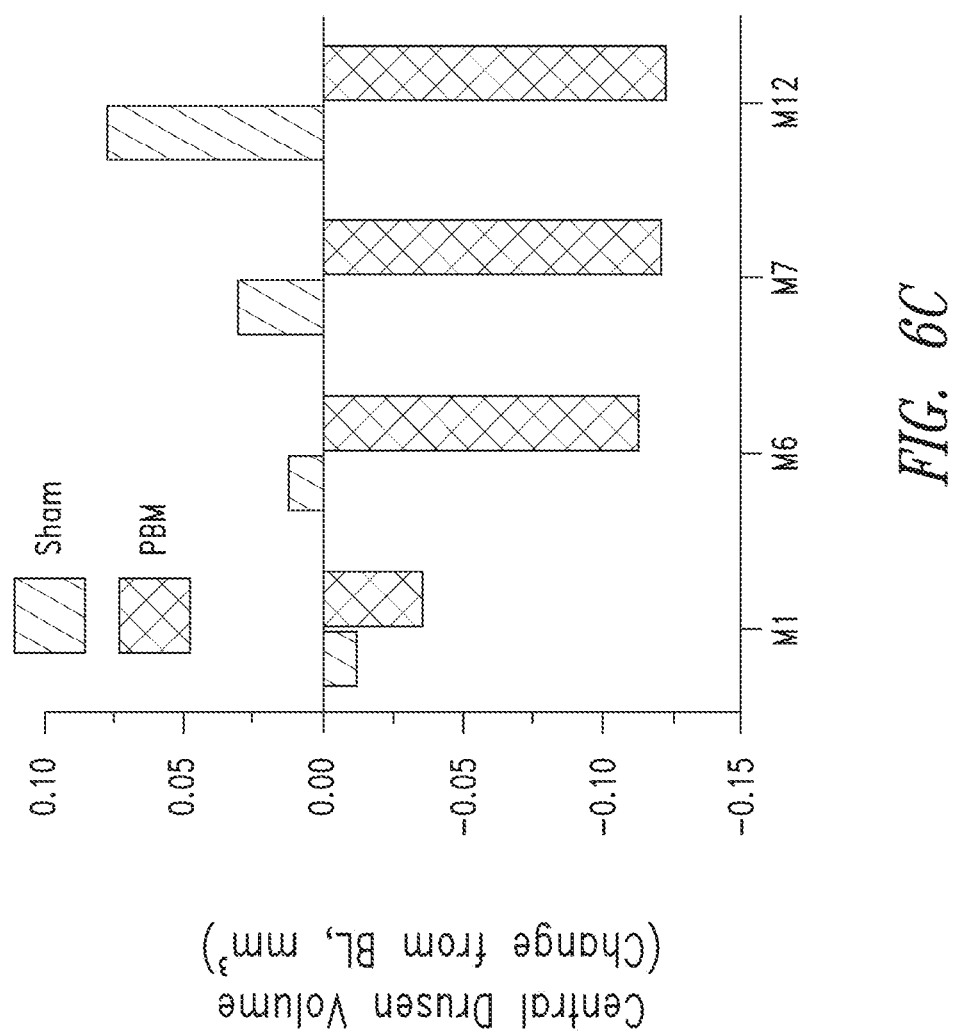
Figure 6D:
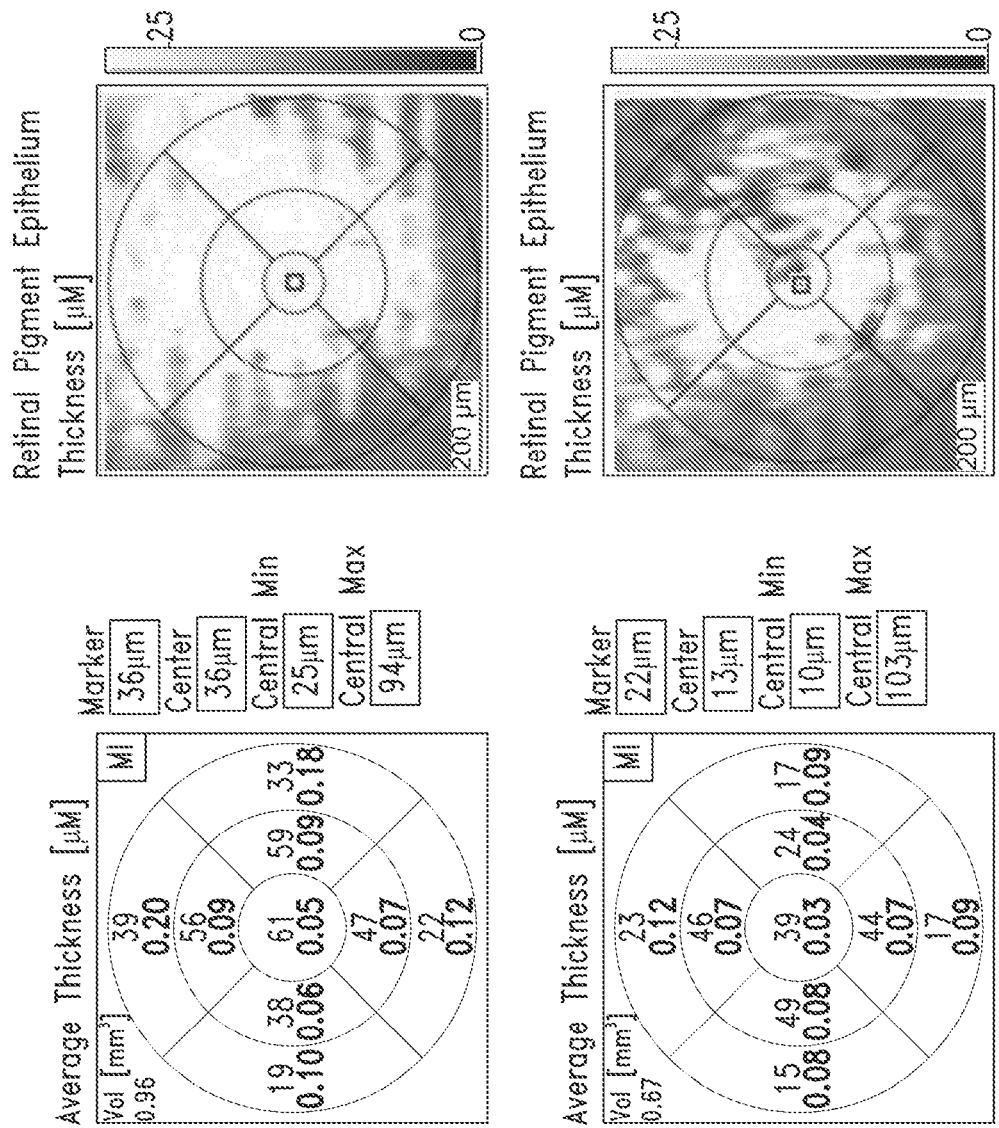
FIGS. 6D-6E show a representative example of anatomical improvement in an eye that was AREDS 3 at baseline and received PBM therapy according to the present disclosure. (6D) (left) Imaging maps illustrating (top) BL drusen volume of 0.78 $mm^3$ with a mean central 1 mm drusen thickness of 165 μm and (bottom) M12 drusen volume of 0.41 $mm^3$ and mean central 1 mm drusen thickness of 18 μm. Black numbers indicate the mean thickness of each ETDRS subgrid and red numbers indicate the corresponding volume (mm3). (Right) Color-coded image showing relative thickness. (6E, 6F) Representative images taken at baseline (top) and M12 (bottom).
Figures 6E, 6F:
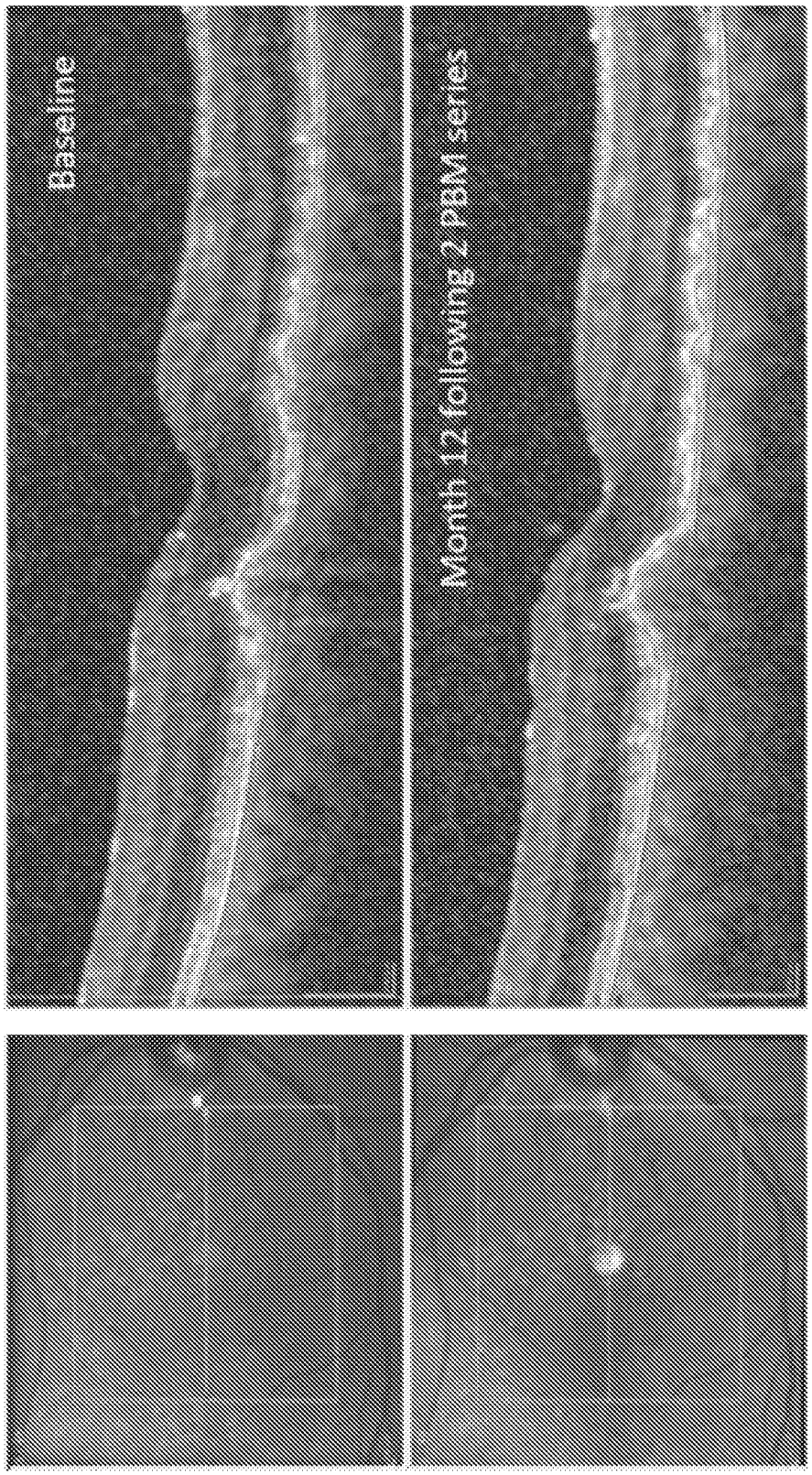

The size and growth of GA was quantitatively assessed by 488 nm FAF, using the Region Finder Analyser (Region Finder Software Heidelberg Engineering, Heidelberg Engineering, Heidelberg, Germany). Schmitz-Valckenberg et al., *Invest. Opthalmol & Vis. Sci.* 52(10):7640-7646 (2011). The area of homogenous hypoautofluorescence on the FAF images at baseline and follow-up images were measured and quantified by one independent masked grader. Schmitz-Valckenberg et al., supra. The absolute GA lesion area was used to evaluate growth rate independent of initial lesion size. See, e.g., Yehoshua et al., *Ophthalmology* 118(4):679-686 (2011). Drusen volume increased over time in 100% of the sham-treated subjects. In contrast, 70% of the PBM-treated subjects showed a decrease in drusen volume. A statistically significant reduction in drusen volume at M12 (LME, p=0.05) was observed in PBM-treated subjects versus the sham-treated subjects (FIG. 6A, 6C). No statistically significant difference in reduction in the mean central 1 mm drusen thickness was observed in PBM-treated subjects versus sham-treated subjects at M12 (LME, p=0.18) (FIG. 6B). Representative images from an AREDS 3 eye that received PBM therapy are provided in FIGS. 6D-6F.

Central 1 mm drusen thickness decreased in all eyes, PBM vs. sham, and was significant at M7 (LME, p=0.03). No difference in terms of GA lesion growth in the PBM-treated subjects compared to the sham-treated subjects following treatment at 12 months was recorded (LME, p>0.05). No statistically significant change in retinal volume or CRT was observed in the PBM- and sham-treated groups.

Example 6

PBM Therapy Improves Patient Outcomes by VFQ-25 Analysis

The National Eye Institute (NEI) sponsored the development of the Visual Function Questionnaire (VFQ-25) to measure the dimensions of self-reported vision-targeted health status that are most important for persons who have chronic eye diseases. The survey measures the influence of visual disability and visual symptoms on generic health domains such as emotional well-being and social functioning, in addition to task-oriented domains related to daily visual functioning. Questions included in the VFQ-25 represent the content identified during a series of condition-specific focus groups with patients who had age-related cataracts, glaucoma, age-related macular degeneration, diabetic retinopathy, or CMV retinitis.

The VFQ-25 questionnaire was given at BL, M3, M7, M9, and M12. A VFQ-25 composite score was determined and further sub analysis was conducted. Overall, the PBM treated subjects demonstrated a statistically significant improvement in composite score (p-value=0.003). Sham treatment did not demonstrate a statistically significant improvement (p-value>0.05). The questionnaire was developed for a broad number of vision diseases, so emphasis was placed on a subset of questions (Q5-Q14) from Part II: Difficulty with activities. General health and driving-related questions (most of the current subjects did not drive) were not evaluated in this study population, as those were considered less relevant. Responses were scored numerically as (1) No difficulty at all, (2) A little difficulty, (3) Moderate difficulty, (4) Extreme difficulty, (5) Stopped doing this because of your eyesight or (6) Stopped doing this for other reasons or not interested in doing this. Questions were further analyzed following the VFQ-25 assessment score chart. Two activities-of-daily-living questions demonstrated statistically significantly improvements for PBM-treated patients (p-values<0.05).

Q8: How much difficulty do you have reading street signs or the names of stores?

Q10: Because of your eyesight, how much difficulty do you have noticing objects off to the side while you are walking along?

Figure 7A:
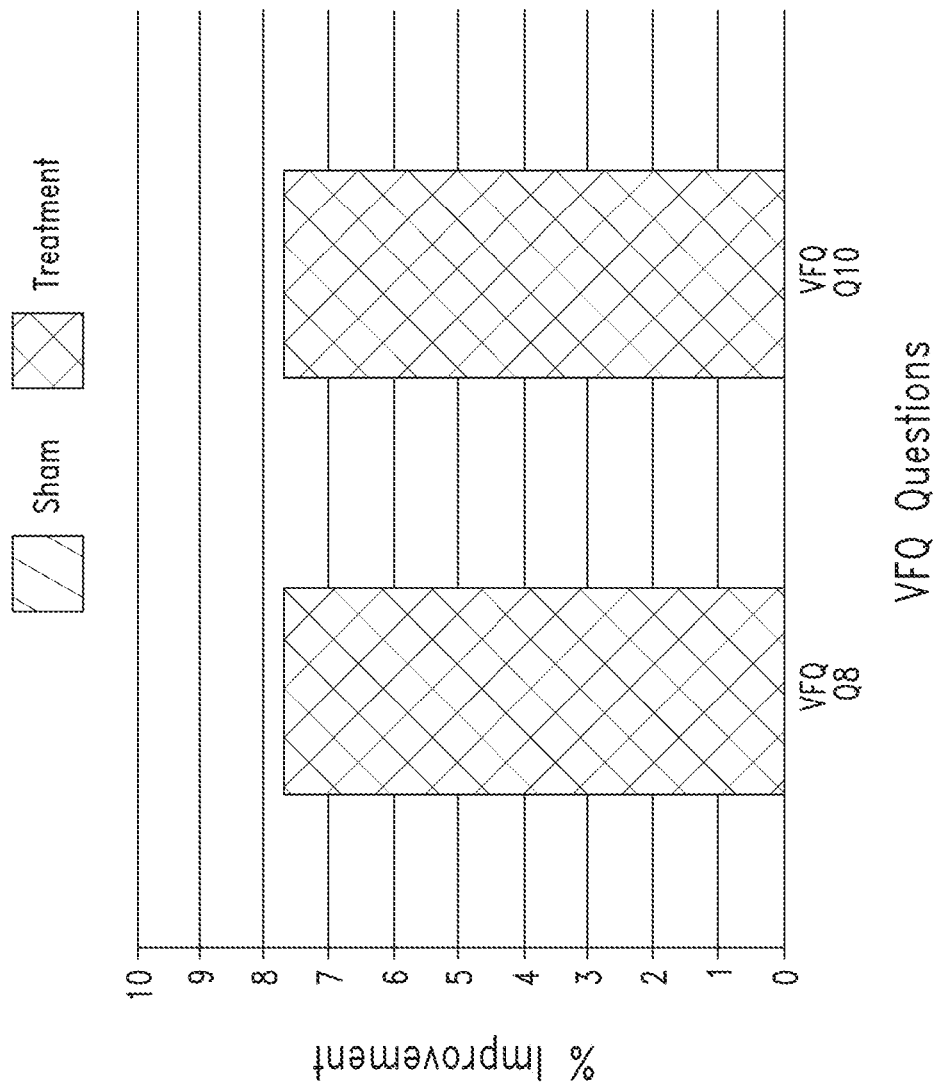
FIGS. 7A and 7B show improvements reported (percentage change in activities of daily living scores at M3 of the trial by patients to questions from the National Eye Institute's VFQ-25 questionnaire. (7A) Improvements reported by PBM-treated patients in response to Questions 8 and 10. (7B) Improvements (or lack thereof) reported by PBM-treated or Sham-treated patients in response to Questions 5, 11, and 14.

Data are shown in FIG. 7A.

Figure 7B:
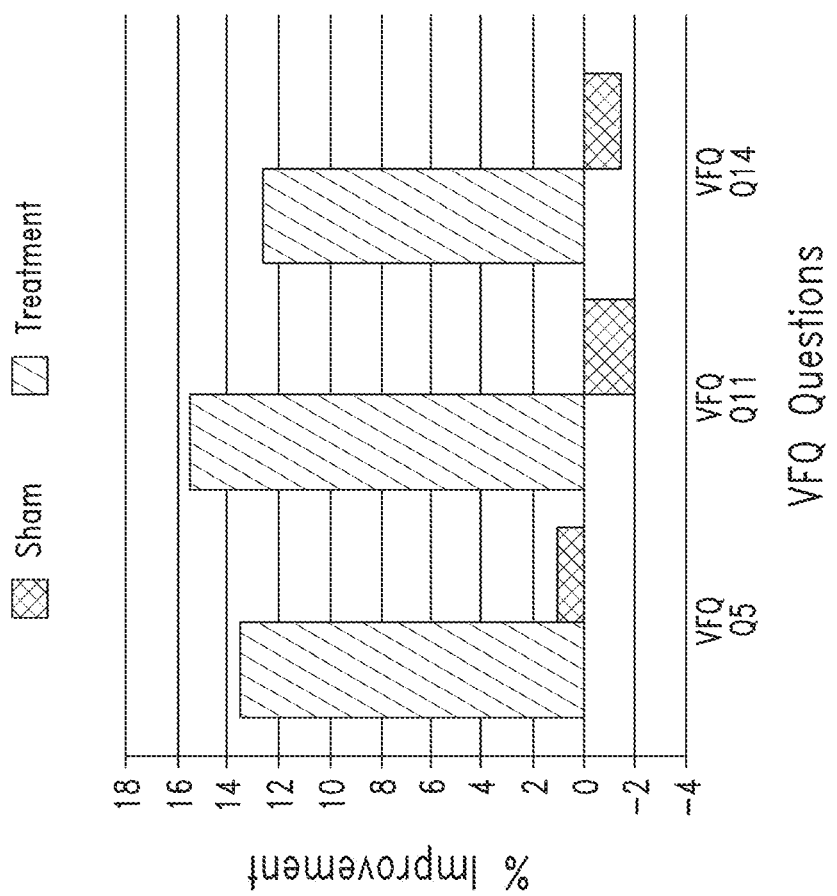

Three additional questions asking about routine activities with varying difficulty provided a 10-15% improvement in score with PBM treatment at 3M, but did not met statistical significance. Data are shown in FIG. 7B. These additional questions were:

Q5: How much difficulty do you have reading ordinary print in newspapers?Would you say you have:

Q11: Because of your eyesight, how much difficulty do you have seeing how people react to things you say?

Q14: Because of your eyesight, how much difficulty do you have going out to see movies, plays, or sorts events?

Overall, the PBM-treated subjects demonstrated a statistically significant improvement in the QoL composite score at M3 (p=0.003), M7 (p=0.015) and M9 (p=0.003) (Wilcoxon signed rank test) and select questions related to activities of daily living at M3, M7 and M9. The sham group did not demonstrate a statistically significant improvement (Wilcoxon signed rank test, p>0.05) in any assessment.

Example 7

Discussion

The present clinical study study evaluated PBM in subjects with dry AMD. The results from the study illustrate positive benefits in both clinical and anatomical outcomes in dry AMD subjects following PBM treatment and informs patient selection for optimizing individualized clinical outcomes.

Significant improvements in BCVA and CS were noted at various timepoints following treatment with PBM. A mean increase of 4 letters in BCVA was observed immediately after the first series of treatments, followed by a decline in this improvement up to the six-month mark, where the second PBM series was scheduled. The subsequent PBM treatment series immediately improved BCVA letter scores, which similarly declined back to BL levels by M12. These data show that repeating PBM treatment at 4-6 month re-treatment intervals can be useful in providing sustained (e.g., continuous or near-continuous) benefits. Overall, 50% of the PBM-treated subjects showed ≥5 letters improvement after the first series of treatment and 46% of PBM-treated subjects showed ≥5 letters improvement after the second series of treatments. When analyzing letter gain in this subject cohort, a total improvement of 8 letters was observed following the initial treatment series. This subject-specific increase in BCVA letter gain following PBM treatment suggests a potential influence of individual disease pathology on the efficacy of PBM treatment.

The majority of subjects enrolled in this study were classified as AREDS category 4 with central GA including foveola involvement. GA with foveola involvement was seen in 67.4% of the subjects. Stratifying eyes by BCVA outcomes into those who were high responders (i.e., ≥5 letters improvement following the first series of treatment at M1, HR) demonstrated that high responding eyes were earlier in the disease stage. In the HR group, 66.7% were AREDS category 3 and 75% had no GA. Notably, 92% of the subjects in the HR group had no GA with central foveola involvement. In contrast, in the PBM-treated low responder group (i.e., <5 letters of improvement at M1, LR), 83.3% were AREDS category 4 with GA and central foveola involvement. Without being bound by theory, as disease progression occurs, increased damage and tissue loss are observed, and may limit the amount of viable retinal tissue that may serve as a substrate for PBM activity. Therefore, these findings show that dry AMD subjects in earlier stages of the disease are more likely to respond better to PBM as compared to subjects with more advanced disease and extensive central tissue loss. The high number of advanced stage AMD subjects contributed to the reduced overall benefits seen in BCVA letter score in the intent to treat group analysis.

Improvements in CS and microperimetry were also noted following PBM. CS and microperimetry are often found to be more sensitive parameters and impaired at an earlier disease stage than BCVA. A significant improvement in CS at level E (18 cycles/degree) was observed immediately following PBM treatment extending to M12. A trend was also noted at level D (12 cycles/degree) over the first 6 months from BL. Improvements in high performing CS subjects support beneficial changes in visual function, regardless of severity. Significant improvements in fixation stability (microperimetry) was also observed. The combined efficacy of PBM to improve aspects of BCVA, CS and microperimetry support the efficacy of PBM on visual function on multiple visual clinical endpoints.

Functional endpoints such as BCVA and CS are standardized clinical outcome measures for the assessment of disease severity, progression and response to treatment (see, e.g., Wu et al., *Ophthalmology* 121(8):1612-1619 (2014)). In AMD, improvements in BCVA are often used as a standard for the assessment of efficacy of new treatment options. In clinical trials for wet AMD, pharmaceutical interventions are employed to recover significant acute vision loss through inhibition of neovascularization. In the earlier stages of AMD and also in GA with foveal sparing, the extent of visual dysfunction may remain stable or slowly decline over years without rapid vision loss. Therefore, visual gains in this patient population, which hasn't experienced rapid profound vision loss due to choroidal neovascularization (CNV), may be clinically relevant.

The results from the present clinical study also revealed improvements in anatomical features such as drusen volume and thickness. Briefly, early and intermediate AMD is sometimes characterized by the thickening of the Bruch membrane due to the accumulation of lipid and proteins, which form sub-RPE deposits called drusen. Increases in the of amount of drusen are correlated to disease progression and are considered to be a risk factor for the development of late complications of AMD including GA, CNV, and subsequent central vision loss. The rate of progression to advanced AMD (CNV and GA over 5 years) has been reported to be 1.3% with many small or few medium drusen, 18% if many medium or any large drusen (=AREDS, category 3) and 43% if unilateral advanced AMD is present (see, e.g., Joachim et al., *Ophthalmology* 122(12):2482-2489 (2015); Chew et al., *JAMA ophthalmology* 132(3):272-277. Currently, there are no approved treatments that act to improve vision and influence drusen number, volume, or thickness. Sham-treated subjects showed an increase in all eyes in drusen volume throughout the study, whereas 70% of PBM-treated eyes showed a reduction in drusen volume.

A validated patient questionnaire (VFQ-25 by the NH/NEI) was used to capture subject-reported improvement in quality of life measures. PBM treatment provided a statistically significant benefit over time, which was consistent with other quantitative clinical outcome measures. Activities of daily living scores were improved that illustrate an enhancement in the quality of life for dry AMD subjects.

A limited number of adverse events (AEs) were reported throughout the study, demonstrating a favorable safety profile of the treatment. A total of 21 AEs were reported during the study by four sham subjects and seven PBM subjects. One eye converted to wet AMD in the PBM-treated group within one month of the study. The rate of conversion from dry to wet in the current 1-year study was 1 out of the 24 PBM-treated eyes for an incident rate of 4.2% or 1 out of 46 eyes for an overall incident rate of 2.2%. The converted subject was treated with intravietral injections in respective eye and followed with no further complications. PBM treatment was continued for the duration of the study in the remaining dry AMD eye. The dry AMD eye in this subject gained 22 letters by M12 following PBM treatments. The rate of progression to CNV was recently reported as 7.4% per patient-year (Chakravarthy et al., *Ophthalmology* 125 (6):842-849 (2018). None of the ocular AEs were considered to be related to the device and common for the type of disease treated.

The present study showed significant improvements following PBM treatment in various parameters including BCVA and CS. Improvements in clinical outcomes following PBM were more robustly seen in subjects with earlier stage disease. In addition, improvements in microperimetry and anatomical outcomes such as drusen volume and drusen thickness were observed. No device-related adverse events were reported demonstrating a favorable safety profile of PBM in Dry AMD. These findings demonstrate the utility of PBM in subjects with dry AMD.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating dry age-related macular degeneration (AMD) in an eye of a subject, comprising:
   administering, to the eye of the subject having dry AMD, a first treatment including multiple sessions delivering an effective amount of photobiomodulation (PBM) light comprising one or more of:
      (i) light having a wavelength in a yellow range;
      (ii) light having a wavelength in a red range; or
      (iii) light having a wavelength in a near-infrared (NIR) range;
   ceasing administration of the first treatment for a first period having a duration of about 4, 5, or 6 months, wherein the duration of the first period is determined according to a nature, state, severity, or progression of disease or condition of the eye of the subject, or a responsiveness of the subject or disease to the first treatment, or one or more measured characteristics of the eye of the subject that is responsive to the first treatment;
   after completion of the first period, administering to the eye of the subject having dry AMD a second treatment including multiple sessions delivering an effective amount of PBM light comprising one or more of:
      (i) light having a wavelength in a yellow range;
      (ii) light having a wavelength in a red range; or
      (iii) light having a wavelength in a near-infrared (NIR) range;
   ceasing administration of the second treatment for a second period having a duration of about 4, 5, or 6 months, wherein the duration of the second period is determined according to a nature, state, severity, or progression of disease or condition of the eye of the subject, or a responsiveness of the subject or disease to the second treatment, or one or more measured characteristics of the eye of the subject that is responsive to the second treatment; and
   after completion of the second period, administering to the eye of the subject having dry AMD a third treatment including multiple sessions delivering an effective amount of PBM light comprising one or more of:
      (i) light having a wavelength in a yellow range;
      (ii) light having a wavelength in a red range; or
      (iii) light having a wavelength in a near-infrared (NIR) range.

2. The method of claim 1, wherein, prior to administering the treatment including an effective amount of PBM light, the eye:
   (iv) had a best corrected visual acuity (BCVA) score of 70 or more;
   (v) had a Snellen BCVA equivalent score of 20/100 or better;
   (vi) had an AREDS categorization of AREDS 1, 2 or 3 or 4;
   (vii) did not have geographic atrophy (GA) with central fovealor involvement; or
   (viii) any combination of (iv)-(vii).

3. The method of claim 1, wherein administering the treatment including an effective amount of PBM light comprises administering to the eye of the subject two or three of:
   (i) the light having a wavelength in the yellow range;
   (ii) the light having a wavelength in the red range; or
   (iii) the light having a wavelength in the near-infrared (NIR) range.

4. The method of claim 1, wherein the wavelength in the yellow range is in a range from 550 nm to 620 nm.

5. The method of claim 4, wherein the wavelength in the yellow range is:
(i) in a range from 560 nm to 610 nm;
(ii) in a range from 570 nm to 600 nm; or
(iii) 590 nm±15 nm.

6. The method of claim 1, wherein the wavelength in the red range is in a range from 620 nm to 750 nm.

7. The method of claim 6, wherein the wavelength in the red range is:
(i) in a range from 650 nm to 720 nm; or
11 670±15 nm.

8. The method of claim 1, wherein the wavelength in the NIR range is in a range from 750 nm to 950 nm.

9. The method of claim 8, wherein the wavelength in the NIR range is:
(i) in a range from 800 nm to 900 nm;
(ii) in a range from 825 nm to 875 nm; or
(iii) 850 nm±15 nm.

10. The method of claim 1, wherein administering the treatment including an effective amount of PBM light comprises administering to the eye of the subject two or three of:
(i) light having a wavelength of 590 nm±15 nm;
(ii) light having a wavelength of 670 nm±15 nm; or
(iii) light having a wavelength of 850 nm±15 nm.

11. The method of claim 1, wherein two or more of the lights are administered to the eye of the subject simultaneously.

12. The method of claim 1, wherein one or more of the lights is administered to the eye of the subject in a pulsed fashion and one or more of the lights is administered to the eye of the subject in a continuous fashion.

13. The method of claim 1, wherein one or more of the lights is administered to the eye of the subject while the eye is open and/or wherein one or more of the lights is administered to the eye of the subject while the eye is closed.

14. The method of claim 1, wherein administering the treatment including an effective amount of PBM light comprises administering to the eye of the subject one or more of:
(i) the light comprising a wavelength in the yellow range for at least 30 seconds;
(ii) the light comprising a wavelength in the red range for at least 75 seconds; or
(iii) the light comprising a wavelength in the near-infrared (NIR) range for at least 30 seconds.

15. The method of claim 1, wherein the PBM light is administered to the eye at least three or four times in a week.

16. The method of claim 1, wherein the eye had previously received an effective amount of PBM light about 6 months prior to the administering of the treatment.

17. The method of claim 1, wherein two or more of the lights are administered to the eye of the subject in a sequence.

18. The method of claim 1, wherein the treatment includes administering the PBM light to the eye at treatment times in a period of at least three or four weeks.

19. A method for treating dry age-related macular degeneration (AMD) in an eye of a subject, comprising:
administering, to the eye of the subject having dry AMD, a treatment including multiple sessions delivering an effective amount of photobiomodulation (PBM) light comprising one or more of:
(i) light having a wavelength in a yellow range;
(ii) light having a wavelength in a red range; or
(iii) light having a wavelength in a near-infrared (NIR) range;
ceasing administration of the PBM light to the eye of the subject having dry AMD for a period of about 1, 2, or 3 months; and
testing the eye of the subject about 1 month after beginning the treatment including the effective amount of PBM light, and
when the eye of the subject having dry AMD has had an increase in a best corrected visual acuity (BCVA) letter score of less than 5 letters as compared to a BCVA letter score of the eye before receiving the treatment, at about 1 to 3 months after the treatment, administering to the eye of the subject having dry AMD another treatment including multiple sessions delivering an effective amount of PBM light comprising one or more of:
(i) light having a wavelength in a yellow range;
(ii) light having a wavelength in a red range; or
(iii) light having a wavelength in a near-infrared (NIR) range.

20. A method for treating dry age-related macular degeneration (AMD), comprising:
administering photobiomodulation (PBM) treatment to an eye of a subject having dry AMD, wherein the PBM treatment is administered according to a predefined schedule that includes at least three cycles of administering PBM treatment to the eye of the subject, and wherein each cycle of administering PBM treatment includes:
administering a treatment comprising multiple sessions delivering an effective amount of PBM light comprising one or more of a wavelength in a yellow range, a wavelength in a red range, or a wavelength in a near-infrared (NIR) range; and
ceasing administration of the PBM treatment for a period having a duration of about 4, 5, or 6 months, wherein the duration of the period is determined according to a nature, state, severity, or progression of disease or condition of the eye of the subject, or a responsiveness of the subject or disease to the treatment, or one or more measured characteristics of the eye of the subject that is responsive to the treatment.

* * * * *